(12) United States Patent
Daifuku et al.

(10) Patent No.: US 11,971,563 B2
(45) Date of Patent: *Apr. 30, 2024

(54) NEAR-INFRARED ABSORBING COMPOSITION, NEAR-INFRARED ABSORBING FILM, AND IMAGE SENSOR FOR SOLID-STATE IMAGING ELEMENT

(71) Applicant: Konica Minolta, Inc., Tokyo (JP)

(72) Inventors: Koji Daifuku, Hino (JP); Yosuke Mizutani, Mitaka (JP); Natsumi Itamoto, Hino (JP); Keigo Tamaki, Fukuroi (JP); Yutaro Horie, Hachioji (JP); Kenji Hayashi, Hachioji (JP); Issei Nakahara, Hino (JP); Takahiko Nojima, Tokyo (JP); Kiyoshi Fukusaka, Fussa (JP)

(73) Assignee: KONICA MINOLTA, INC., Tokyo (JP)

( * ) Notice: Subject to any disclaimer, the term of this patent is extended or adjusted under 35 U.S.C. 154(b) by 898 days.

This patent is subject to a terminal disclaimer.

(21) Appl. No.: 16/981,195

(22) PCT Filed: Mar. 11, 2019

(86) PCT No.: PCT/JP2019/009571
§ 371 (c)(1),
(2) Date: Sep. 15, 2020

(87) PCT Pub. No.: WO2019/181587
PCT Pub. Date: Sep. 26, 2019

(65) Prior Publication Data
US 2021/0026053 A1 Jan. 28, 2021

(30) Foreign Application Priority Data
Mar. 23, 2018 (JP) .................. 2018-055498

(51) Int. Cl.
| | |
|---|---|
| G02B 5/20 | (2006.01) |
| C07C 305/10 | (2006.01) |
| C07F 9/09 | (2006.01) |
| C07F 9/40 | (2006.01) |
| H01L 27/146 | (2006.01) |

(52) U.S. Cl.
CPC ............ *G02B 5/208* (2013.01); *C07C 305/10* (2013.01); *C07F 9/09* (2013.01); *C07F 9/40* (2013.01); *H01L 27/1462* (2013.01)

(58) Field of Classification Search
CPC ......... G02B 5/208; C07C 305/10; C07F 9/09; C07F 9/40; H01L 27/1462
See application file for complete search history.

(56) References Cited

U.S. PATENT DOCUMENTS

| | | | | |
|---|---|---|---|---|
| 2007/0042194 | A1* | 2/2007 | Hayashi | ............ B32B 17/10036 428/426 |
| 2015/0138369 | A1* | 5/2015 | Takakuwa | .............. G02B 5/208 427/160 |

FOREIGN PATENT DOCUMENTS

| | | | |
|---|---|---|---|
| CN | 104937453 A | 9/2015 | |
| EP | 1496375 B1 * | 10/2008 | ............... G02B 5/20 |
| JP | 2002-006101 A | 1/2002 | |
| JP | 4422866 B2 | 2/2010 | |
| JP | 4684393 B2 | 5/2011 | |
| JP | 4926699 B2 | 5/2012 | |
| JP | 2015-043063 A | 3/2015 | |
| JP | 5890805 B2 | 3/2016 | |
| WO | 2014/126192 A1 | 8/2014 | |

OTHER PUBLICATIONS

KIPO, Office Action/Search Report for the related Korean Application No. 10-2020-7026095, dated Mar. 7, 2022, with English translation.
PCT, International Preliminary Report on Patentability for the corresponding application No. PCT/JP2019/009571, dated Sep. 29, 2020, with English translation.
JPO, Office Action/Search Report for the related Japanese Application No. 2020-508211, dated May 17, 2022, with English translation.
CNIPA, Office Action/Search Report for the related Chinese Application No. 201980020396.7, dated Oct. 21, 2021, with English translation.
PCT, International Search Report for the corresponding application No. PCT/JP2019/009571, dated Jun. 4, 2019, with English translation.

* cited by examiner

Primary Examiner — Jane L Stanley
(74) Attorney, Agent, or Firm — Lucas & Mercanti, LLP

(57) ABSTRACT

Disclosed is a near-infrared absorbing composition, including: a near-infrared absorbing agent; and a solvent, wherein the near-infrared absorbing agent includes at least one of the following Component (A) and Component (B):
Component (A): a component composed of a compound having a structure of the following general formula (I) and a metal ion;
Component (B): a component composed of a metal complex that is obtainable by a reaction of the compound having the structure of the following general formula (I) and a metal compound.

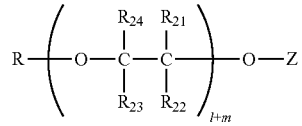

General Formula (I)

11 Claims, 1 Drawing Sheet

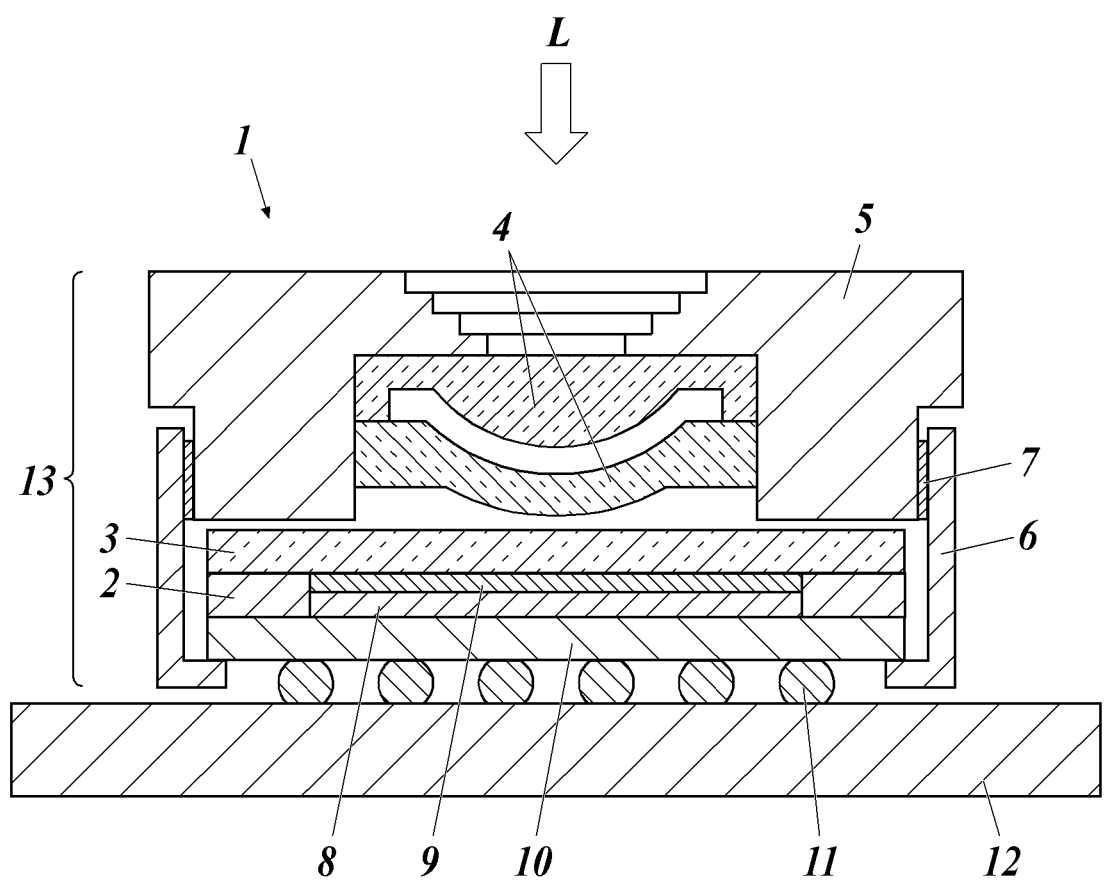

NEAR-INFRARED ABSORBING COMPOSITION, NEAR-INFRARED ABSORBING FILM, AND IMAGE SENSOR FOR SOLID-STATE IMAGING ELEMENT

CROSS REFERENCE TO RELATED APPLICATION

This Application is a 371 of PCT/JP2019/009571 filed on Mar. 11, 2019, which claims priority of Japanese patent application no. 2018-055498 filed Mar. 23, 2018, the above applications are incorporated herein by reference.

TECHNICAL FIELD

The present invention relates to a near-infrared absorbing composition, and a near-infrared absorbing film and an image sensor for a solid imaging element using the same. In more detail, the present invention relates to a near-infrared absorbing composition with good dispersion of the metal complex, in particular the copper complex, and good dispersion stability when exposed to water (resistance to moisture), a near-infrared absorbing film using the composition, and an image sensor for a solid imaging element with the near-infrared absorbing film.

BACKGROUND

In recent years, a CCD or CMOS imaging sensor, either of which is a solid imaging element for color images, has been used in video cameras, digital still cameras, camera phones. Since a silicon photodiode sensitive to light in the near-infrared wavelength range is used in a light receiver of such solid imaging elements, it is required to correct the luminous efficiency. For this purpose, a near-infrared cutoff filter is often used.

With regard to the materials of such near-infrared cutoff filters, in recent years, near-infrared absorbing compositions using a phosphonic acid copper complex have been disclosed (e.g. see Patent Document 1 to Patent Document 3).

These patent documents aim an improvement in quality, e.g. an improvement in storage stability, by using a single solvent in Patent Document 1, a single specific solubilizer in Patent Document 2 or a single specific solvent in Patent Document 3 as a dispersion medium of the phosphonic acid copper complex. While all the patent documents focus on the stability of the near-infrared absorbing compositions after a binder resin component is added to the phosphonic acid copper complex, they do not mention the stability of the near-infrared absorbing compositions in the absence of any binder component. In this regard, a study by the present inventors revealed that the dispersion stability of a near-infrared absorbing composition before addition of a binder resin has a great influence on the quality of a final product.

On the other hand, a problem with copper complexes is aggregation that occurs in water-containing systems, even in dispersions with no binder or films with a binder. Further, such aggregation is accelerated by heat. Patent Document 4 discloses an optical filter with a near-infrared absorbing layer that contains a copper complex obtained by a reaction of a phosphate compound having an ethylene oxide structure or a propylene oxide structure with a copper compound. However, it was revealed that even when such a copper complex is used, dispersion of the copper complex and the dispersion stability when exposed to water (resistance to moisture) are insufficient.

CITATION LIST

Patent Documents

[Patent Document 1] JP-B 4684393
[Patent Document 2] JP-B 4926699
[Patent Document 3] JP-B 5890805
[Patent Document 4] JP-B 4422866

SUMMARY OF INVENTION

Problems to be Solved by Invention

The present invention has been made in view of the above-described problems and circumstances, and an object thereof relates to a near-infrared absorbing composition that has good near-infrared absorption performance, improved dispersion of the metal complex, in particular the copper complex, and improved dispersion stability when exposed to water (resistance to moisture), and to a near-infrared absorbing film formed from the composition, and an image sensor for a solid imaging element with the near-infrared absorbing film.

Means to Solve the Problems

In order to achieve the above-described object, the present inventors conducted a study on the cause of the above-described problems. As a result, they found that a near-infrared absorbing composition that has good near-infrared absorption performance, good dispersion of the metal complex of the near-infrared absorbing composition, and improved dispersion stability when exposed to water (resistance to moisture), a near-infrared absorbing film formed from the composition, and an image sensor for a solid imaging element with the near-infrared absorbing film can be achieved by a near-infrared absorbing composition that contains a near-infrared absorbing agent and a solvent, in which the near-infrared absorbing agent contains at least one of Component (A) and Component (B), where Component (A) is composed of a compound having a structure of the following general formula (I) and a metal ion, and Component (B) is a metal complex that is a reaction product of the compound having the structure of the following general formula (I) with a metal compound. The present invention has been thus made.

That is, the above-described problems of the present invention are solved by the following means.

1. A near-infrared absorbing composition, comprising: a near-infrared absorbing agent; and a solvent,
    wherein the near-infrared absorbing agent comprises at least one of the following Component (A) and Component (B),
    Component (A): a component composed of a compound having a structure of the following general formula (I) and a metal ion; and
    Component (B): a component composed of a metal complex that is a reaction product of the compound having the structure of the following general formula (I) and a metal compound.

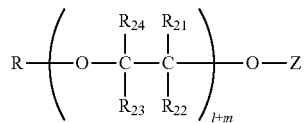

General Formula (I)

In the general formula (I), R is an alkyl group of 1 to 20 carbons or an aryl group of 6 to 20 carbons, in which R may have a substituent, and z is a structural unit selected from the following formulae (Z-1) to (Z-3).

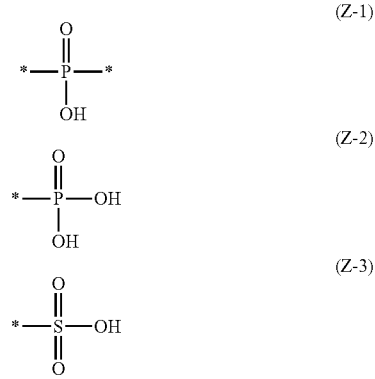

The asterisk in the formulae (Z-1) to (Z-3) represents a bonding site that is bonded to O of the general formula (I).

$R_{21}$ to $R_{24}$ each is a hydrogen atom or an alkyl group of 1 to 4 carbons.

The compound having the structure of the general formula (I) has at least one moiety satisfying the Condition (i) and at least one moiety satisfying the Condition (iii) concurrently.

Condition (i): $R_{21}$ to $R_{24}$ are all hydrogen atoms.

Condition (ii): at least one of $R_{21}$ to $R_{24}$ is an alkyl group of 1 to 4 carbons.

In the general formula (I), l is the number of the moiety satisfying the Condition (i) and is from 1 to 10. m is the number of the moiety satisfying the Condition (ii) and is from 1 to 10.

2. The near-infrared absorbing composition according to item 1, wherein metal of the metal ion or the metal complex is copper.
3. The near-infrared absorbing composition according to item 1 or 2, wherein the compound having the structure of the general formula (I) is a compound having a structure of the following general formula (II).

General Formula (II)

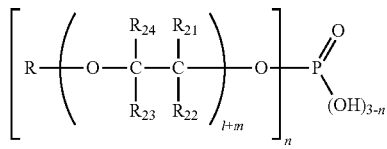

In the general formula (II), R, $R_{21}$ to $R_{24}$, l and m are as defined in the general formula (I). n is one or two, and when n is two, the structures in the parentheses may be the same or different.

4. The near-infrared absorbing composition according to any one of items 1 to 3, wherein the compound having the structure of the general formula (I) has a monoester and a diester, and a molar ratio of the mono ester is within the range of 20% to 95%.
5. The near-infrared absorbing composition according to any one of items 1 to 4, wherein the general formula (I) concurrently has at least one moiety satisfying the following Condition (i) and at least one moiety satisfying the following Condition (iii).

Condition (i): $R_{21}$ to $R_{24}$ are all hydrogen atoms.

Condition (iii): One of $R_{21}$ to $R_{24}$ is an alkyl group of 1 to 4 carbons, and the other three are hydrogen atoms.

6. The near-infrared absorbing composition according to any one of items 1 to 5, wherein l and m in the general formula (I) are each within a range of 1 to 3.
7. The near-infrared absorbing composition according to any one of items 1 to 6, wherein an average particle size of the metal complex is equal to or less than 50 nm.
8. The near-infrared absorbing composition according to any one of items 1 to 7, further comprising a phosphonic acid compound.
9. The near-infrared absorbing composition according to any one of items 1 to 8, further comprising a near-infrared absorption adjuster having an maximum absorption wavelength within a wavelength range of 650 nm to 800 nm.
10. The near-infrared absorbing composition according to any one of items 1 to 9, comprising acetic acid within a range of 1 mol % to 100 mol % with respect to metal of the metal ion or the metal compound.
11. A near-infrared absorbing film using the near-infrared absorbing composition according to any one of items 1 to 10.
12. An image sensor for a solid imaging element, comprising the near-infrared absorbing film according to item 11.

Advantageous Effects of Invention

By the above-described means of the present invention, it is possible to provide a near-infrared absorbing composition with good dispersion of the metal complex, in particular the copper complex, and improved dispersion stability when exposed to water (resistance to moisture), a near-infrared absorbing film formed from the composition, and an image sensor for a solid imaging element with the near-infrared absorbing film.

It has not become completely clear how the advantageous effects of the present invention is produced and exerted, however it is presumed as follows.

The near-infrared absorbing composition of the present invention contains a near-infrared absorbing agent and a solvent and is characterized in that the near-infrared absorbing agent contains at least one of the following Component (A) and Component (B).

Component (A): a component composed of a compound having the structure of the general formula (I) and a metal ion Component (B): a component composed of a metal complex that is a reaction product of the compound having the structure of the general formula (I) with a metal compound In the near-infrared absorbing composition of the present invention, it is presumed that the metal complex, which is formed by a reaction of the compound having the structure of the general formula (I) with the metal compound, exhibits near-infrared absorbing properties with high absorbance index. Characteristically, the compound having the structure of the general formula (I) has not only an ethylene oxide structure (Condition (i)) but also an alkyl-substituted ethylene oxide structure (Condition (ii)). Compared to an ethylene oxide structure, an alkyl-substituted ethylene oxide structure has higher diastereomer components due to the presence of the substituents ($R_{21}$ to $R_{24}$) in the compound having the structure of the general formula (I). Accordingly, aggregation is inhibited by the entropy effect, which allows higher dispersion stability when exposed to water. In addition, the hydrophobic effect by the substituents ($R_{21}$ to $R_{24}$) further increases the dispersion stability.

If the compound has only the alkyl-substituted ethylene oxide structure (Condition (ii)), the substituents ($R_{21}$ to $R_{24}$) would sterically hinder smooth formation of the complex with the metal, and fine dispersion of the metal complex could not be achieved. In contrast, since the compound having the structure of the general formula (I) further has the ethylene oxide structure in the same compound structure (Condition (i)), fine dispersion of the metal complex can be achieved. It is presumed that such fine dispersion can provide visible light transmittance.

It is presumed that this is the mechanism how the near-infrared absorbing composition with good dispersion of the metal complex and good dispersion stability when exposed to water (high resistance to moisture) is achieved.

When a compound having only the alkyl-substituted ethylene oxide structure and a compound having only the ethylene oxide structure are used in combination to form a metal complex with a metal ion, the compound having only the ethylene oxide structure preferentially form a complex with the metal. As a result, the dispersion stability when exposed to water cannot be improved. To achieve the object of the present invention, it is important to have both the ethylene oxide structure and the alkyl-substituted ethylene oxide structure in the same molecule.

In the present invention, a copper complex, particularly a phosphate copper complex is a preferred copper complex in terms of better dispersion and better near-infrared cutoff stability.

Furthermore, it is preferred to contain a ligand that can form a complex with a copper ion. In particular, it is preferred to use a phosphonic acid compound in combination as the ligand in terms of obtaining the near-infrared absorbing composition with better stability over time, e.g. dispersion stability of copper complex particles and near-infrared cutoff stability.

BRIEF DESCRIPTION OF DRAWINGS

FIG. 1 is a schematic cross-sectional view of a camera module including a solid imaging element with the near-infrared absorbing film of the present invention, illustrating an example configuration thereof.

DESCRIPTION OF EMBODIMENTS

The near-infrared absorbing composition of the present invention includes a near-infrared absorbing agent and a solvent, wherein the near-infrared absorbing agent contains at least one of Component (A) and Component (B), where Component (A) is composed of a compound having a structure of the above general formula (I) and a metal ion, and Component (B) is a metal complex that is a reaction product of the compound having the structure of the above general formula (I) with a metal compound. This characteristic is a technical feature common to the following embodiments.

In the near-infrared absorbing composition of the present invention, in terms of obtaining the objective advantageous effects of the present invention, it is preferred that the metal of the metal ion or the metal complex is copper since it is possible to obtain better near-infrared absorption performance, better dispersion of the metal complex and better dispersion stability when exposed to water (resistance to moisture).

It is preferred that the compound having the structure of the general formula (I) is a compound having the structure of the general formula (II) since it is possible to further improve the dispersion stability when exposed to water.

It is preferred that the compound having the structure of the general formula (I) has a monoester and a diester, wherein the molar percentage of the monoester is within the range of 20% to 95% since it is possible to further improve the dispersion of the metal complex and the dispersion stability in storage in various conditions.

It is preferred that the general formula (I) has at least one moiety satisfying the Condition (i) and at least one moiety satisfying the Condition (iii) concurrently since it is possible to further improve the dispersion and the dispersion stability when exposed to water (resistance to heat and moisture).

It is preferred that the average particle size of the metal complex is equal to or less than 50 nm since it is possible to achieve better visible transmittance and better absorption of near-infrared light.

It is preferred that l and m of the general formula (I) are each within the range of 1 to 3 since it is possible to further improve the dispersion of the metal complex and the dispersion stability in storage in various conditions.

It is preferred that the composition contains a phosphonic acid compound since it is possible to achieve better dispersion stability (resistance to heat and moisture), better visible transmittance and better absorption performance of near-infrared light.

It is preferred that the composition contains a near-infrared absorption adjuster having a maximum absorption wavelength within the wavelength range of 650 nm to 800 nm since it is possible to achieve better near-infrared absorption performance.

It is preferred that the composition contains acetic acid within the range of 1 mol % to 100 mol % with respect to the metal content since it is possible to achieve better durability (resistance to heat and moisture) and a desired spectrum.

The present invention and the components thereof, as well as the configurations and the embodiments to carry out the invention, will be detailed in the following. As used herein, the term "to" for a numerical range is intended to mean that numerical values before and after the term are included as the lower and upper limits of the numerical range.

Configuration of Near-Infrared Absorbing Composition

The near-infrared absorbing composition of the present invention is characterized by containing a near-infrared absorbing agent and a solvent, wherein the near-infrared absorbing agent contains at least one of Component (A) and Component (B), which are described later.

Hereinafter, details of the components of the near-infrared absorbing composition of the present invention will be described.

Near-Infrared Absorbing Agent

The near-infrared absorbing agent of the present invention is characterized by containing at least one of the following Component (A) and Component (B).

Component (A) is composed of a compound having a structure of the following general formula (I) and a metal ion.

Component (B) is composed of a metal complex that is a reaction product of the compound having the structure of the following general formula (I) and a metal compound.

Hereinafter, the compound of the general formula (I), which is a representative component of the near-infrared absorbing composition of the present invention, the metal complex, the solvent, and the like will be described. However, the present invention is not limited to the example configurations illustrated herein.

Compound Having Structure of General Formula (I)

First, the compound having the structure of the following general formula (I) will be described.

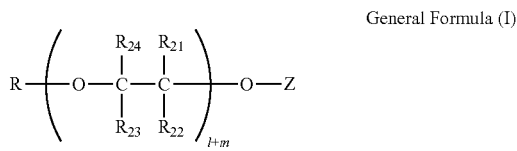

General Formula (I)

In the general formula (I), R is an alkyl group of 1 to 20 carbons or an aryl group of 6 to 20 carbons, and R may have a substituent.

Z is a structural unit selected from the following formulae (Z-1), (Z-2) and (Z-3).

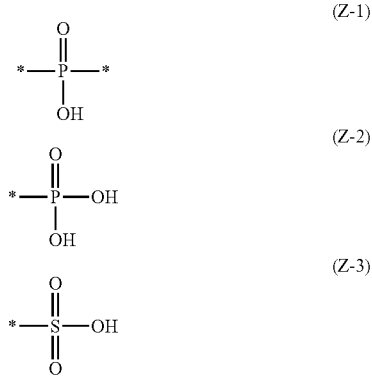

The symbol "* (asterisk)" in the above formulae (Z-1) to (Z-3) represents a bonding site that is bonded to the O of the above general formula (I).

The structural unit selected from the above (Z-1), (Z-2) and (Z-3) is preferably (Z-1) or (Z-2) in terms of dispersion of the metal complex.

In the above general formula (I), when Z is (Z-1), the structural unit is a diester. When Z is (Z-2) or (Z-3), the structural unit is a monoester. In terms of dispersion of the metal complex, the diester and the monoester are preferably present as a mixture. Of the monoester and the diester, the molar percentage of the monoester is preferably within the range of 20% to 95%.

In the general formula (I), l is the number of moieties that satisfies the Condition (i) described later, which ranges from 1 to 10. m is the number of moieties that satisfies the Condition (ii) described later, which ranges from 1 to 10.

In the above general formula (I), the alkyl group of 1 to 20 carbons of R may be a straight or branched chain. Examples of such alkyl groups include a methyl group, an ethyl group, an n-propyl group, an isopropyl group, an n-butyl group, a tert-butyl group, an n-hexyl group, a 2-ethylhexyl group, an n-octyl group, a 2-butyloctyl group, a 2-hexyloctyl group, an n-decyl group, a 2-hexyldecyl group, an n-dodecyl group, an n-stearyl group, and the like. Each alkyl group may further have a substituent. In terms of dispersion of the metal complex and the resistance to moisture, R is preferably an alkyl group of 6 to 16 carbons.

Examples of aryl groups of 6 to 20 carbons of R include a phenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group, a biphenylyl group and the like. Preferred are a phenyl group, a naphthyl group, a fluorenyl group, a phenanthryl group, a biphenylyl group and a fluorononyl group. Each aryl group may further have a substituent.

Examples of substituents that R may have include, for example, an alkyl group (e.g. a methyl group, an ethyl group, a trifluoromethyl group, an isopropyl group, etc.), an alkoxy group (e.g. a methoxy group, an ethoxy group, etc.), a halogen atom (e.g. a fluorine atom), a cyano group, a nitro group, a dialkylamino group (e.g. a dimethylamino group), a trialkylsilyl group (e.g. a trimethylsilyl group), a triarylsilyl group (e.g. a triphenylsilyl group, etc.), a triheteroarylsilyl group (e.g. a tripyridylsilyl group), a benzyl group, an aryl group (e.g. a phenyl group), a heteroaryl group (e.g. a pyridyl group, a carbazolyl group, etc.). Examples of condensed rings include 9,9'-dimethylfluorene, carbazole, dibenzofuran, etc. However, the substituent is not particularly limited.

In the above general formula (I), $R_{21}$ to $R_{24}$ are each a hydrogen atom or an alkyl group of 1 to 4 carbons. Examples of such alkyl groups include a methyl group, an ethyl group, an n-propyl group and an n-butyl group. In terms of dispersion of the metal complex, a methyl group is particularly preferred.

The compound having the structure of the general formula (I) according to the present invention is characterized by having at least one moiety satisfying the following Condition (i) and at least one moiety satisfying the Condition (ii) concurrently in its molecular structure.

Condition (i): $R_{21}$ to $R_{24}$ are all hydrogen atoms.

Condition (ii): At least one of $R_{21}$ to $R_{24}$ is an alkyl group of 1 to 4 carbons.

In the moiety satisfying the Condition (ii), at least one of $R_{21}$ to $R_{24}$ is an alkyl group of 1 to 4 carbons. Such moieties include structures in which two of them are such alkyl groups, three of them are such alkyl groups, or all four of them are such alkyl groups. In terms of dispersion of the metal complex, it is preferred that only one of them is an alkyl group of 1 to 4 carbons.

The moiety satisfying the Condition (i) is an ethylene oxide structure in which $R_{21}$ to $R_{24}$ are all hydrogen atoms. Such a moiety has high ability of forming a complex with a metal and contributes to improving the dispersion. In contrast, the moiety satisfying the Condition (ii) is an alkyl-substituted ethylene oxide structure. Such a moiety has a larger number of components and contributes to improving the dispersion stability when exposed to water.

In general formula (I), l is the number of moieties in which $R_{21}$ to $R_{24}$ are all hydrogen atoms as defined by the Condition (i), which ranges from 1 to 10, preferably ranges from 1 to 3. m is the number of moieties in which at least one of $R_{21}$ to $R_{24}$ is an alkyl group of 1 to 4 carbons as defined by the Condition (ii), which ranges from 1 to 10, preferably ranges from 1 to 3.

l and m represent respectively the average numbers of moles added of the ethylene oxide structures and the alkyl-substituted ethylene oxide structures.

It is preferred that the compound having the structure of the above general formula (I) has at least one moiety satisfying the Condition (i) and at least one moiety satisfying the Condition (iii) concurrently.

Condition (i): $R_{21}$ to $R_{24}$ are all hydrogen atoms.

Condition (iii): One of $R_{21}$ to $R_{24}$ is an alkyl group of 1 to 4 carbons, and the other three are hydrogen atoms.

For example, when the alkyl group of the Condition (iii) is a methyl group, the compound has an ethylene oxide structure and propylene oxide structure in the same structure.

As used herein, an "ethylene oxide structure" refers to a repeating structural unit of polyethylene oxide, i.e. an opened ring structure of ethylene oxide or three-membered cyclic ether. Further, an "propylene oxide structure" refers to a repeating structural unit of polypropylene oxide, i.e. an opened ring structure of propylene oxide or three-membered cyclic ether.

It is more preferred that the compound having the structure of the above general formula (I) is a phosphate having the structure of the following general formula (II).

General Formula (II)

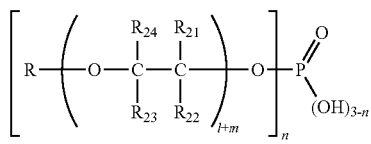

In the general formula (II), R, $R_{21}$ to $R_{24}$, l and m are as defined in the above general formula (I). n is one or two, and when n is two, the structures in the parentheses may be the same or different.

Next, specific examples of the compound having the structure of the general formula (I) will be described.

First, an example of the structure of a typical exemplary compound will be described.

(Exemplary Compound 1)

As shown in Table I below, Exemplary Compound 1 has the structure as follows.

R: methyl group

Condition (i): $R_{21}$ to $R_{24}$=H

Condition (ii): $R_{21}$=H, $R_{22}$=methyl group, $R_{23}$=methyl group, and $R_{24}$=H

Z: Z-3 l: 1.0 m: 8.0

For example, Exemplary Compound 1 is represented by the structure of the following Exemplary Compound (1-1).

Exemplary Compound (1-1)

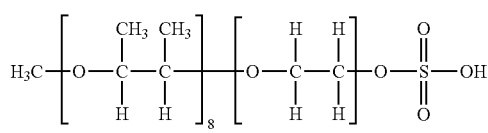

In Exemplary Compound (1-1), the order of the ethylene oxide structure and alkyl-substituted ethylene oxide structures is suitably changeable by changing the synthesis method. That is, the following Exemplary Compound (1-2) is also included in Exemplary Compound 1.

Exemplary Compound (1-2)

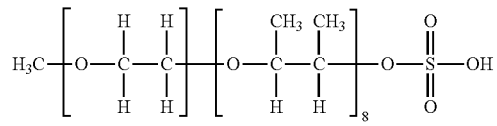

In the present invention, the order of the ethylene oxide structure(s) and the alkyl-substituted ethylene oxide structure(s) is not particularly limited, and compounds having randomly arranged structures are also included in the compounds according to the present invention.

(Exemplary Compound 2)

As shown in Table I below, Exemplary Compound 2 has the structure as follows:

R: methyl group

Condition (i): $R_{21}$ to $R_{24}$=H

Condition (ii): $R_{21}$=H, $R_{22}$=methyl group, $R_{23}$=methyl group, and $R_{24}$=H

Z: Z-1, Z-2 l: 2.0 m: 3.0

Exemplary Compound 2 is represented by Exemplary Compound (2-1) where Z is Z-2 and Exemplary Compound (2-2) where Z is Z-1

Exemplary Compound (2-1)

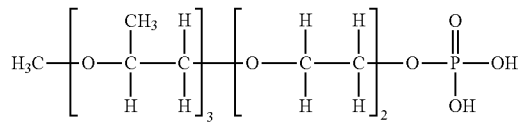

Exemplary Compound (2-2)

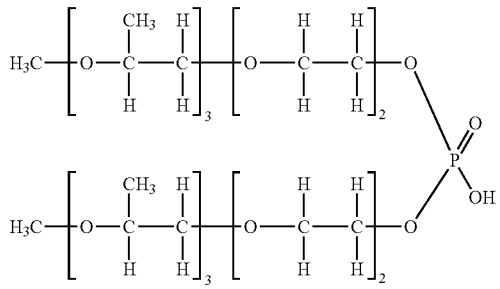

Exemplary Compound 2 has a monoester percentage of 50% and includes Exemplary Compound (2-1) and Exemplary Compound (2-2) in equal molar quantities.

As in the above Exemplary Compound 1, the order of the ethylene oxide structures and the alkyl-substituted ethylene oxide structures in Exemplary Compound 2 is suitably changeable by changing the synthesis method. That is, the following Exemplary Compounds (2-3) and (2-4) are also included in Exemplary Compound 2.

Exemplary Compound (2-3)

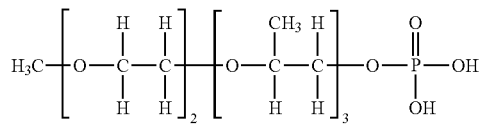

Exemplary Compound (2-4)

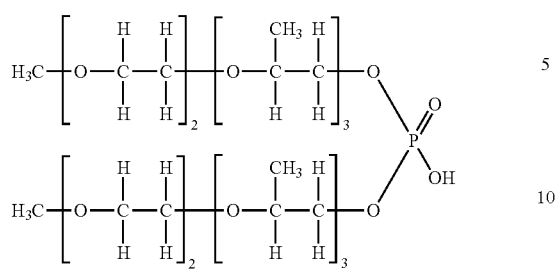

In the present invention, the order of the ethylene oxide structure(s) and the alkyl-substituted ethylene oxide structure(s) is not particularly limited, and compounds having randomly arranged structures are also included in the compounds according to the present invention.

Next, specific examples of the compound having the structure of the general formula (I) are listed in Tables I to IV below, but the present invention is not limited to these exemplified compounds.

General Formula (I)

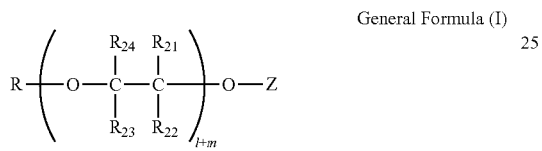

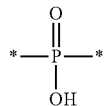
(Z-1)

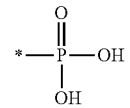
(Z-2)

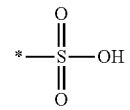
(Z-3)

TABLE I

| Exemplary Compound Number | R | Moiety of Condition (i) | | Moiety of Condition (ii) | | | | | | Monoester ratio (%) |
|---|---|---|---|---|---|---|---|---|---|---|
| | | l | $R_{21}$~$R_{24}$ | m | $R_{21}$ | $R_{22}$ | $R_{23}$ | $R_{24}$ | Z | |
| 1 | methyl | 1.0 | H | 8.0 | H | methyl | methyl | H | Z-3 | — |
| 2 | methyl | 2.0 | H | 3.0 | H | H | methyl | H | Z-1, Z-2 | 50 |
| 3 | methyl | 3.0 | H | 3.0 | H | H | methyl | H | Z-1, Z-2 | 70 |
| 4 | methyl | 1.5 | H | 1.5 | H | H | ethyl | H | Z-1, Z-2 | 50 |
| 5 | methyl | 2.0 | H | 3.0 | H | H | methyl | H | Z-3 | — |
| 6 | ethyl | 1.0 | H | 3.0 | H | H | methyl | H | Z-1, Z-2 | 30 |
| 7 | ethyl | 4.0 | H | 3.0 | H | H | methyl | H | Z-1, Z-2 | 50 |
| 8 | ethyl | 3.0 | H | 3.0 | H | H | methyl | H | Z-1, Z-2 | 50 |
| 9 | ethyl | 2.5 | H | 2.5 | H | H | methyl | H | Z-1, Z-2 | 80 |
| 10 | ethyl | 3.0 | H | 5.0 | methyl | H | H | H | Z-3 | — |
| 11 | n-propyl | 2.0 | H | 4.0 | H | H | methyl | H | Z-1, Z-2 | 40 |
| 12 | n-propyl | 3.0 | H | 8.0 | H | H | methyl | H | Z-1, Z-2 | 50 |
| 13 | n-propyl | 1.5 | H | 1.5 | H | H | methyl | H | Z-1, Z-2 | 70 |
| 14 | n-propyl | 3.0 | H | 2.0 | methyl | H | methyl | H | Z-1, Z-2 | 50 |
| 15 | n-propyl | 2.0 | H | 2.0 | H | H | methyl | H | Z-3 | — |
| 16 | isopropyl | 2.0 | H | 3.0 | H | H | methyl | H | Z-1, Z-2 | 10 |
| 17 | isopropyl | 4.0 | H | 5.0 | methyl | H | methyl | H | Z-1, Z-2 | 20 |
| 18 | isopropyl | 2.0 | H | 2.0 | H | H | methyl | H | Z-1, Z-2 | 80 |
| 19 | n-butyl | 1.0 | H | 1.0 | H | H | methyl | H | Z-1, Z-2 | 30 |
| 20 | n-butyl | 3.0 | H | 3.0 | H | H | methyl | H | Z-1, Z-2 | 50 |
| 21 | n-butyl | 2.0 | H | 4.0 | H | H | methyl | H | Z-1, Z-2 | 50 |
| 22 | n-butyl | 2.5 | H | 2.0 | H | H | methyl | H | Z-1, Z-2 | 80 |
| 23 | n-butyl | 3.0 | H | 3.0 | ethyl | H | H | H | Z-3 | — |

TABLE II

| Exemplary Compound Number | R | Moiety of Condition (i) | | Moiety of Condition (ii) | | | | | Monoester ratio (%) |
|---|---|---|---|---|---|---|---|---|---|
| | | l | $R_{21}$~$R_{24}$ | m | $R_{21}$ | $R_{22}$ | $R_{23}$ | $R_{24}$ | Z | |
| 24 | isobutyl | 3.0 | H | 3.0 | H | H | methyl | H | Z-1, Z-2 | 50 |
| 25 | isobutyl | 6.0 | H | 6.0 | H | H | methyl | H | Z-1, Z-2 | 50 |
| 26 | isobutyl | 2.0 | H | 2.0 | H | H | methyl | H | Z-1, Z-2 | 50 |
| 27 | tert-butyl | 1.5 | H | 2.5 | H | H | methyl | H | Z-1, Z-2 | 50 |
| 28 | tert-butyl | 3.0 | H | 3.0 | H | H | methyl | H | Z-1, Z-2 | 50 |
| 29 | tert-butyl | 2.0 | H | 2.0 | H | H | methyl | H | Z-3 | — |
| 30 | n-pentyl | 3.0 | H | 4.0 | H | H | methyl | H | Z-1, Z-2 | 50 |
| 31 | n-pentyl | 1.0 | H | 2.0 | H | H | methyl | H | Z-1, Z-2 | 50 |
| 32 | n-pentyl | 2.0 | H | 2.0 | H | H | methyl | H | Z-1, Z-2 | 50 |
| 33 | n-pentyl | 3.0 | H | 3.0 | H | H | methyl | H | Z-1, Z-2 | 50 |
| 34 | n-pentyl | 3.0 | H | 3.0 | H | H | methyl | methyl | Z-1, Z-2 | 50 |
| 35 | isopentyl | 3.0 | H | 3.0 | H | H | methyl | H | Z-1, Z-2 | 50 |
| 36 | isopentyl | 8.0 | H | 8.0 | H | H | methyl | H | Z-1, Z-2 | 50 |
| 37 | isopentyl | 2.0 | H | 2.0 | H | H | methyl | H | Z-1, Z-2 | 50 |
| 38 | n-hexyl | 3.0 | H | 3.0 | H | H | methyl | H | Z-1, Z-2 | 60 |
| 39 | n-hexyl | 1.5 | H | 1.5 | H | H | methyl | H | Z-1, Z-2 | 50 |
| 40 | n-hexyl | 5.0 | H | 5.0 | methyl | H | methyl | H | Z-1, Z-2 | 98 |
| 41 | n-hexyl | 2.0 | H | 2.5 | H | H | methyl | H | Z-1, Z-2 | 60 |
| 42 | n-hexyl | 1.0 | H | 1.0 | H | H | methyl | H | Z-1, Z-2 | 70 |
| 43 | n-hexyl | 2.0 | H | 1.0 | H | H | methyl | H | Z-1, Z-2 | 60 |
| 44 | n-hexyl | 1.0 | H | 3.0 | H | H | methyl | H | Z-1, Z-2 | 50 |
| 45 | n-hexyl | 2.0 | H | 4.0 | H | H | methyl | H | Z-3 | — |
| 46 | isohexyl | 1.2 | H | 1.2 | H | H | methyl | H | Z-1, Z-2 | 50 |
| 47 | isohexyl | 2.0 | H | 2.0 | H | H | methyl | H | Z-1, Z-2 | 50 |
| 48 | n-octyl | 5.0 | H | 5.0 | H | H | methyl | H | Z-1, Z-2 | 50 |
| 49 | n-octyl | 2.0 | H | 2.0 | H | H | methyl | H | Z-1, Z-2 | 50 |
| 50 | n-octyl | 1.0 | H | 2.0 | H | H | methyl | H | Z-1, Z-2 | 50 |

TABLE III

| Exemplary Compound Number | R | Moiety of Condition (i) | | Moiety of Condition (ii) | | | | | Monoester ratio (%) |
|---|---|---|---|---|---|---|---|---|---|
| | | l | $R_{21}$~$R_{24}$ | m | $R_{21}$ | $R_{22}$ | $R_{23}$ | $R_{24}$ | Z | |
| 51 | n-octyl | 3.0 | H | 3.0 | H | H | methyl | H | Z-1, Z-2 | 50 |
| 52 | n-octyl | 2.0 | H | 1.0 | H | H | methyl | H | Z-1, Z-2 | 60 |
| 53 | n-octyl | 2.0 | H | 2.0 | H | H | methyl | H | Z-1, Z-2 | 55 |
| 54 | 2-ethylhexyl | 2.0 | H | 2.0 | H | H | methyl | H | Z-1, Z-2 | 40 |
| 55 | 2-ethylhexyl | 3.0 | H | 3.0 | H | H | methyl | H | Z-1, Z-2 | 30 |
| 56 | 2-ethylhexyl | 2.5 | H | 2.5 | H | H | methyl | H | Z-1, Z-2 | 50 |
| 57 | 2-ethylhexyl | 1.0 | H | 1.5 | H | H | methyl | H | Z-1, Z-2 | 60 |
| 58 | 2-ethylhexyl | 1.0 | H | 2.0 | methyl | H | H | H | Z-1, Z-2 | 30 |
| 59 | 2-ethylhexyl | 3.0 | H | 1.0 | H | H | methyl | H | Z-3 | — |
| 60 | isooctyl | 5.0 | H | 5.0 | methyl | H | methyl | H | Z-1, Z-2 | 18 |
| 61 | isooctyl | 1.2 | H | 1.8 | H | H | methyl | H | Z-1, Z-2 | 50 |
| 62 | isooctyl | 3.0 | H | 2.0 | H | H | methyl | H | Z-1, Z-2 | 50 |
| 63 | isooctyl | 2.0 | H | 3.0 | H | H | methyl | H | Z-1, Z-2 | 50 |
| 64 | n-decyl | 3.0 | H | 3.0 | H | H | methyl | H | Z-1, Z-2 | 50 |
| 65 | n-decyl | 2.0 | H | 2.0 | H | H | methyl | H | Z-1, Z-2 | 50 |
| 66 | n-decyl | 3.0 | H | 1.0 | H | H | methyl | H | Z-1, Z-2 | 50 |
| 67 | n-decyl | 1.0 | H | 1.0 | H | H | methyl | H | Z-1, Z-2 | 50 |
| 68 | n-decyl | 2.0 | H | 5.0 | methyl | methyl | H | H | Z-1, Z-2 | 95 |
| 69 | n-decyl | 3.0 | H | 3.0 | H | H | methyl | H | Z-3 | — |
| 70 | isodecyl | 3.0 | H | 3.0 | H | H | methyl | H | Z-1, Z-2 | 50 |
| 71 | isodecyl | 2.0 | H | 2.0 | H | H | methyl | H | Z-1, Z-2 | 50 |
| 72 | n-dodecyl | 1.0 | H | 1.5 | H | H | methyl | H | Z-1, Z-2 | 50 |
| 73 | n-dodecyl | 2.0 | H | 2.0 | H | H | methyl | H | Z-1, Z-2 | 60 |
| 74 | n-dodecyl | 1.0 | H | 1.0 | H | H | methyl | H | Z-1, Z-2 | 50 |
| 75 | n-dodecyl | 1.3 | H | 1.7 | H | H | methyl | H | Z-1, Z-2 | 30 |
| 76 | n-dodecyl | 5.0 | H | 5.0 | H | H | butyl | H | Z-1, Z-2 | 50 |
| 77 | n-dodecyl | 2.0 | H | 2.0 | H | H | methyl | H | Z-1, Z-2 | 60 |

TABLE IV

| Exemplary Compound Number | R | Moiety of Condition (i) 1 | Moiety of Condition (i) $R_{21}$~$R_{24}$ | Moiety of Condition (ii) m | Moiety of Condition (ii) $R_{21}$ | Moiety of Condition (ii) $R_{22}$ | Moiety of Condition (ii) $R_{23}$ | Moiety of Condition (ii) $R_{24}$ | Z | Monoester ratio (%) |
|---|---|---|---|---|---|---|---|---|---|---|
| 78 | 2-butyloctyl | 1.0 | H | 1.0 | H | H | methyl | H | Z-1, Z-2 | 50 |
| 79 | 2-butyloctyl | 1.0 | H | 2.0 | H | H | methyl | H | Z-1, Z-2 | 50 |
| 80 | 2-butyloctyl | 2.0 | H | 2.0 | H | H | methyl | H | Z-1, Z-2 | 50 |
| 81 | 2-butyloctyl | 3.0 | H | 3.0 | H | H | methyl | H | Z-1, Z-2 | 50 |
| 82 | 2-butyloctyl | 3.0 | H | 3.0 | methyl | H | H | H | Z-1, Z-2 | 50 |
| 83 | 2-hexyloctyl | 2.0 | H | 2.0 | H | H | methyl | H | Z-1, Z-2 | 50 |
| 84 | 2-hexyloctyl | 2.0 | H | 3.0 | H | H | methyl | H | Z-1, Z-2 | 30 |
| 85 | 2-hexyloctyl | 3.0 | H | 3.0 | H | H | methyl | H | Z-1, Z-2 | 50 |
| 86 | 2-hexyloctyl | 3.0 | H | 1.0 | H | H | methyl | H | Z-1, Z-2 | 70 |
| 87 | n-pentadecyl | 3.0 | H | 2.0 | H | H | methyl | H | Z-1, Z-2 | 50 |
| 88 | n-pentadecyl | 2.0 | H | 3.0 | H | H | methyl | H | Z-1, Z-2 | 50 |
| 89 | n-pentadecyl | 3.0 | H | 3.0 | H | H | methyl | H | Z-1, Z-2 | 50 |
| 90 | n-pentadecyl | 1.0 | H | 1.0 | H | H | methyl | H | Z-1, Z-2 | 50 |
| 91 | n-stearyl | 3.0 | H | 3.0 | H | H | methyl | H | Z-1, Z-2 | 70 |
| 92 | n-stearyl | 1.2 | H | 2.4 | H | H | methyl | H | Z-1, Z-2 | 70 |
| 93 | n-stearyl | 5.0 | H | 5.0 | H | H | methyl | H | Z-1, Z-2 | 60 |
| 94 | n-stearyl | 3.0 | H | 3.0 | H | H | methyl | H | Z-1, Z-2 | 50 |
| 95 | n-stearyl | 3.0 | H | 3.0 | H | H | methyl | H | Z-3 | — |
| 96 | phenyl | 3.0 | H | 3.0 | H | H | methyl | H | Z-1, Z-2 | 50 |
| 97 | phenyl | 2.0 | H | 2.0 | H | H | methyl | H | Z-1, Z-2 | 50 |
| 98 | phenyl | 1.0 | H | 1.0 | H | H | methyl | H | Z-1, Z-2 | 50 |
| 99 | xylyl | 3.0 | H | 3.0 | H | H | methyl | H | Z-1, Z-2 | 50 |

Compounds having the structure of the general formula (I) according to the present invention can be synthesized by referring to known methods such as those described in JP-A 2005-255608, JP-A 2015-000396, JP-A 2015-000970, JP-A 2015-178072, JP-A 2015-178073 and JP-B 4422866.

Synthesis of Exemplary Compounds

Next, representative examples of synthesis of the compounds having the structure of general formula (I) according to the present invention will be described. However, the present invention is not limited to the illustrated synthesis methods.

Synthesis of Exemplary Compound 49 n-octanol (130 g, 1.0 mol) was charged in an autoclave. With a potassium hydroxide catalyst at a pressure of 147 kPa and a temperature of 130° C., addition of 116 g (2.0 mol) of propylene oxide was caused, and thereafter addition of 88 g (2.0 mol) of ethylene oxide was caused.

Then, after checking no residual n-octanol was present, the adduct was transferred to a reaction vessel and reacted with 47 g (0.33 mol) of phosphonic anhydride in toluene at 80° C. for 5 hours. The product was washed with distilled water, and the solvent was distilled away under reduced pressure. Thus, the following Exemplary Compound 49 (R=octyl group, Condition (i): $R_{21}$=H, $R_{22}$=H, $R_{23}$=H, $R_{24}$=H, Condition (ii): $R_{21}$=H, $R_{22}$=H, $R_{23}$=methyl group, $R_{24}$=H, l: 2.0, m: 2.0, Z: phosphonic monoester (Z-2)/phosphonic diester (Z-1)) was obtained.

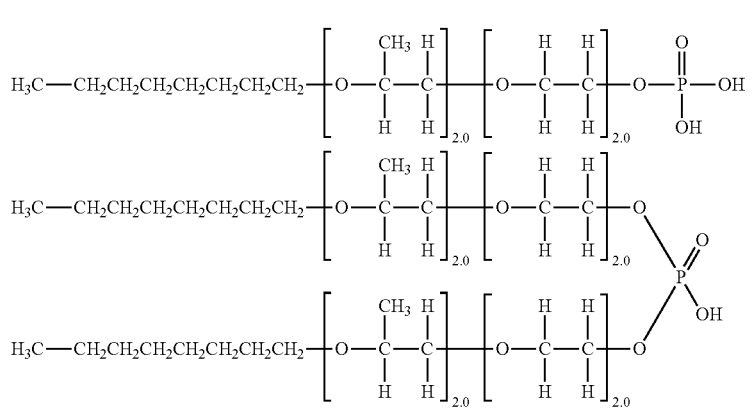

Exemplary Compound 49

Synthesis of Exemplary Compound 56

2-ethylhexanol (130 g, 1.0 mol) was charged in an autoclave. With a potassium hydroxide catalyst at a pressure of 147 kPa and a temperature of 130° C., addition of 145 g (2.5 mol) of propylene oxide was caused, and thereafter addition of 110 g (2.5 mol) of ethylene oxide was caused.

Then, after checking no residual 2-ethylhexanol was present, the adduct was transferred to a reaction vessel and reacted with 47 g (0.33 mol) of phosphonic anhydride in toluene at 80° C. for 5 hours. The product was washed with distilled water, and the solvent was distilled away under reduced pressure. Thus, the following Exemplary Compound 56 (R=2-ethylhexyl group, Condition (i): $R_{21}$=H, $R_{22}$=H, $R_{23}$=H, $R_{24}$=H, Condition (ii): $R_{21}$=H, $R_{22}$=H, $R_{23}$=methyl group, $R_{24}$=H, l: 2.5, m: 2.5, Z: phosphonic monoester (Z-2)/phosphonic diester (Z-1)) was obtained.

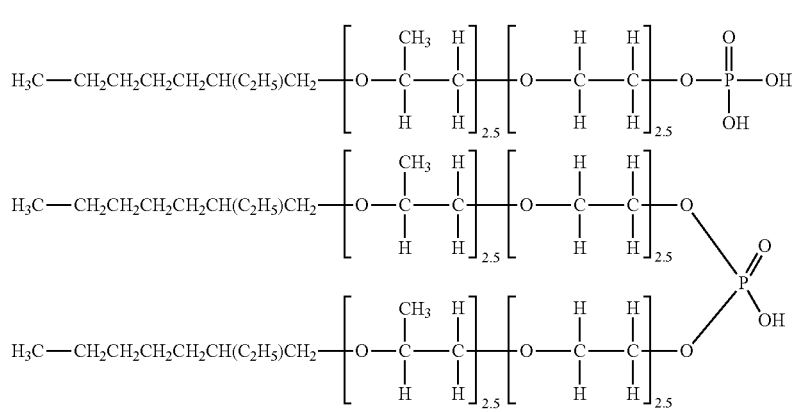

Exemplary Compound 56

Synthesis of Exemplary Compound 59

2-ethylhexanol (130 g, 1.0 mol) was charged in an autoclave. With a potassium hydroxide catalyst at a pressure of 147 kPa and a temperature of 130° C., addition of 58 g (1.0 mol) of propylene oxide was caused, and thereafter addition of 132 g (3.0 mol) of ethylene oxide was caused.

Then, after checking no residual 2-ethylhexanol was present, the adduct was transferred to a reaction vessel and reacted with 117 g (1.0 mol) of chlorosulfonic acid in toluene at 80° C. by adding the chlorosulfonic acid dropwise over one hour. The product was washed with distilled water, and the solvent was distilled away under reduced pressure. Thus, the following Exemplary Compound 59 (R=2-ethylhexyl group, Condition (i): $R_{21}$=H, $R_{22}$=H, $R_{23}$=H, $R_{24}$=H, Condition (ii): $R_{21}$=H, $R_{22}$=H, $R_{23}$=methyl group, $R_{24}$=H, l: 3.0, m: 1.0, Z: sulfonic acid (Z-3)) was obtained.

ion is used. Examples of such copper salts include copper salts of organic acid such as anhydrous copper acetate, anhydrous copper formate, anhydrous copper stearate, anhydrous copper benzoate, anhydrous copper acetoacetate, anhydrous copper ethyl acetoacetate, anhydrous copper methacrylate, anhydrous copper pyrophosphate, anhydrous copper naphthenate, and anhydrous copper citrate; hydrates of the copper salts of organic acid; copper salts of inorganic acid such as copper oxide, copper chloride, copper sulfate, copper nitrate, copper phosphate, basic copper sulfate, and basic copper carbonate; hydrates of the copper salts of inorganic acid; and copper hydroxide.

Metal Complex

The metal complex obtainable by a reaction of the compound having the structure of the general formula (I) and a

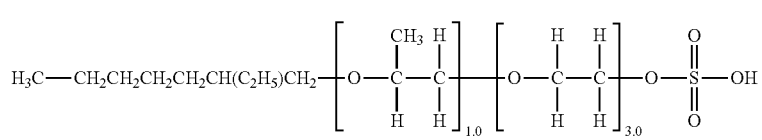

Exemplary Compound 59

Metal Components

As described above, the near-infrared absorbing agent according to the present invention is characterized by containing at least one of Component (A) and Component (B), where Component (A) is composed of the compound having the structure of the general formula (I) and a metal ion, and Component (B) is composed of a metal complex that is a reaction product of the compound having the structure of the general formula (I) and a metal compound.

Examples of metal species that can be used for the metal ion of the component (A) or the metal complex of the component (B) include mono or multivalent metals of Groups I to VIII of the periodic table that can form a complex. Specifically, examples of such metals include aluminum, cobalt, chromium, copper, iron, magnesium, manganese, nickel, tin, titanium, zinc, and the like. Among them, nickel, copper, chromium, cobalt and zinc are preferred, and copper is most preferred.

In the near-infrared absorbing agent according to the present invention, the metal species is preferably applied as a complex. In the case of copper, which is a typical example thereof, a copper salt capable of supplying a divalent copper metal compound according to the present invention can be synthesized by a method described in, for example, JP-B 4422866 or JP-B 5953322.

The general formula (I) according to the present invention binds to a metal ion by a coordination bond and/or an ionic bond via a phosphonic acid group or a sulfonic acid group of Z. The metal ion is surrounded by the general formula (I) and is dissolved or dispersed in the near-infrared absorbing film. When the metal species is copper ion, which is a typical example, near-infrared light is selectively absorbed as a result of electronic transition between d orbitals of the copper ion. When Z is a phosphonic acid group, which is a typical example, the content of phosphorous atom in the near-infrared absorbing film is preferably equal to or less than 1.5 with respect to 1 mol of copper ion. Further, it was confirmed that a very preferred range is from 0.3 to 1.3. That is, it is very preferred that the content ratio of phosphorous atom to copper ion (hereinafter referred to as "P/Cu") ranges from 0.3 to 1.3 in molar ratio in terms of the resistance to moisture of the near-infrared absorbing film and dispersion of the copper ion in the near-infrared absorbing film.

When the P/Cu is less than 0.3 in molar ratio, the copper ion that coordinates with the compound of general formula (I) is excessive. This tends to cause less uniform dispersion of the copper ion in the near-infrared absorbing film. When the P/Cu is greater than 1.3 in molar ratio, transparency is more likely to be lost. This tends to occur when the near-infrared absorbing film is thin and the copper ion content is high, and the tendency is particularly remarkable in a high-temperature and high-humidity environment. It is more preferred that the P/Cu is within the range of 0.8 to 1.3 in molar ratio. When the molar ratio is equal to or greater than 0.8, dispersion of copper ion in resin can be surely and sufficiently improved.

When the content of copper ion in the near-infrared absorbing film is less than the above-described lower limit, it is more likely to be difficult to achieve sufficient near-infrared absorption. This occurs when the thickness of the near-infrared absorbing film is less than approximately 1 mm. When the content of copper ion is greater than the above-descried upper limit, it is more likely to be difficult to disperse copper ion in the near-infrared absorbing film.

Acetic Acid

It is preferred that the near-infrared absorbing composition of the present invention contains acetic acid within the range of 1 mol % to 100 mol % with respect to the metal ion of Component (A) or the metal of the metal compound of the metal complex of Component (B) of the near-infrared absorbing agent.

For example, acetic acid is produced when a copper complex compound is prepared from the general formula (I) and copper acetate. It is preferred that the amount of the acetic acid falls within the above-described range in terms of durability (resistance to heat and moisture) and obtaining a desired spectrum in the near-infrared region.

Average Particle Size of Metal Complex

The metal complex according to the present invention has an average particle size of preferably 1 to 200 nm, more preferably 1 to 100 nm, and particularly preferably 1 to 50 nm.

For example, the average particle size of a metal complex as used in the present invention can be determined by the dynamic light scattering method using the zeta potential/particle size measuring system ELSZ-1000ZS (Otsuka Electronics, Co., Ltd.) as a measuring device.

Alternatively, the average particle size can be determined by a method that involves taking an electron micrograph of metal complex particles by a transmission electron microscope (at a magnification of 500000 to 2000000), measuring the projection areas of the particles, measuring the diameters of circles equivalent to the measured areas, which are performed for 100 particles, and calculating the arithmetic average as the average particle size.

Phosphonic Acid Compounds, Phosphoric Acid Compounds, Sulfonic Acid Compounds and the Metal Complexes Thereof It is preferred that the near-infrared absorbing composition of the present invention contains a phosphonic acid compound, a phosphonic acid compound, a sulfonic acid compound or a metal complex thereof, particularly a phosphonic acid as described below.

Phosphoric Acid Compounds

Examples of phosphonic acid compounds include:
1) methyl phosphate;
2) ethyl phosphate;
3) n-propyl phosphate;
4) i-propyl phosphate;
5) n-butyl phosphate;
6) t-butyl phosphate;
7) n-pentyl phosphate;
8) n-hexyl phosphate;
9) 2-ethylhexyl phosphate;
10) n-heptyl phosphate;
11) n-octyl phosphate;
12) cyclohexyl phosphate;
and the like.

Sulfonic Acid Compounds

Examples of sulfonic acid compounds include compounds described in JP-A 2015-430638 and the like.

Phosphonic Acid Compounds

It is preferred that the near-infrared absorbing composition of the present invention contains a phosphonic acid compound having the structure of the following general formula (1).

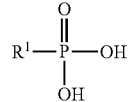

General Formula (1)

In the above general formula (1), R' is a branched, linear or cyclic alkyl, alkenyl, alkynyl, aryl or aryl group of 1 to 30 carbons, wherein at least one hydrogen atom may or may not be substituted with a halogen atom, an oxyalkyl, polyoxyalkyl, oxyaryl, oxyaryl, polyoxyaryl, acyl, aldehyde, carboxyl or hydroxyl group, or a group having an aromatic ring.

Examples of phosphonic acid compounds having the structure of the general formula (1) include ethyl phosphonic acid, propylphosphonic acid, butylphosphonic acid, pentylphosphonic acid, hexyl phosphonic acid, and octylphosphonic acid, 2-ethylhexylphosphonic acid, 2-chloroethylphosphonic acid, 3-bromopropylphosphonic acid, 3-methoxybutylphosphonic acid, 1,1-dimethylpropylphosphonic acid, 1,1-dimethylethylphosphonic acid, 1-methylpropylphosphonic acid, benzene phosphonic acid, 4-methoxyphenylphosphonic acid, and the like. Some examples are shown as the following compounds (H-1) to (H-8).

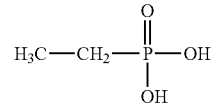

(H-1)

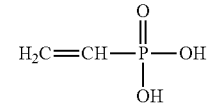

(H-2)

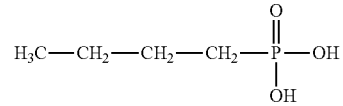

(H-3)

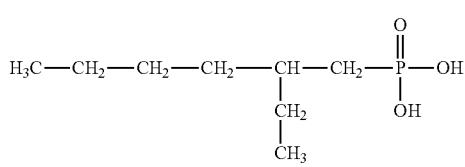

(H-4)

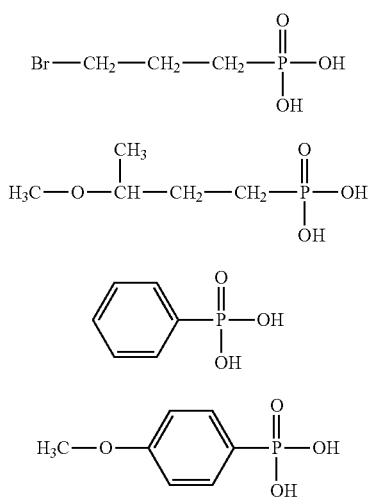

In the present invention, it is preferred that the phosphonic acid of the copper phosphonate complex is at least one alkyl phosphonic acid selected from the following group of phosphonic acids.

1: Methylphosphonic acid
2: Ethylphosphonic acid
3: Propylphosphonic acid
4: Butylphosphonic acid
5: Pentylphosphonic acid
6: Hexylphosphonic acid
7: Octylphosphonic acid
8: 2-ethylhexylphosphonic acid
9: 2-chroloethylphosphonic acid
10: 3-bromophosphonic acid
11: 3-methoxybutylphosphonic acid
12: 1,1-dimethylpropylphosphonic acid
13: 1,1-dimethylethylphosphonic acid
14: 1-methylpropylphosphonic acid Phosphonic Acid Metal Complex Next, phosphonic acid metal complex suitable for the present invention will be described.

In the present invention, examples of metals of the phosphonic acid metal complex include mono- or multivalent metals that belongs to Group I to XIV of the periodic table and can form a complex. Specifically, examples of such metals include aluminum, cobalt, chromium, copper, iron, magnesium, manganese, nickel, tin, titanium, zinc, and the like. Among them, nickel, copper, chromium, cobalt and zinc are preferred, and copper is most preferred.

Hereinafter, copper phosphonate complex applicable to the present invention will be described as representative examples. The copper phosphonate complex has the structure of the following general formula (2).

General Formula (2)

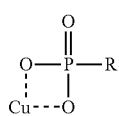

In the general formula (2), R is an alkyl, phenyl or benzyl group.

Copper salts that can be a source of a divalent copper ion are used for forming the copper phosphonate complex having the structure of the general formula (2) Examples of such copper salts include copper salts of organic acids such as anhydrous copper acetate, anhydrous copper formate, anhydrous copper stearate, anhydrous copper benzoate, anhydrous copper acetoacetate, anhydrous copper ethyl acetoacetate, anhydrous copper methacrylate, anhydrous copper pyrophosphate, anhydrous copper naphthenate and anhydrous copper citrate; hydrates of the copper salts of organic acids; copper salts of inorganic acids such as copper oxide, copper chloride, copper sulfate, copper nitrate, copper phosphate, basic copper sulfate and basic copper carbonate; hydrates of the copper salts of inorganic acids; and copper hydroxide.

In the present invention, it is preferred that the phosphonic acid of the copper phosphonate complex is an alkylphosphonic acid. Examples of such copper phosphonate complexes include copper ethylphosphonate complex, copper propylphosphonate complex, and copper butylphosphonate complex, copper pentylphosphonate complex, copper hexylphosphonate complex, copper octylphosphonate complex, copper 2-ethylhexylphosphonate complex, copper 2-chloroethylphosphonate complex, copper 3-bromopropylphosphonate complex, copper 3-methoxybutylphosphonate complex, copper 1,1-dimethylpropylphosphonate complex, copper 1,1-dimethylethylphosphonate complex, copper 1-methylpropylphosphonate complex, and the like.

Solvent

Next, solvents that can be used for preparing the near-infrared absorbing composition of the present invention will be described.

The solvent that is used for the near-infrared absorbing composition of the present invention is not particularly limited. Such solvents include hydrocarbon solvents. Specifically, preferred examples include aliphatic hydrocarbon solvents, aromatic hydrocarbon solvents, and halogenated solvents.

Examples of aliphatic hydrocarbon solvents include non-cyclic aliphatic hydrocarbon solvents such as hexane and heptane, cyclic aliphatic hydrocarbon solvents such as cyclohexane, alcohol solvents such as methanol, ethanol, n-propanol and ethylene glycol, ketone solvents such as acetone and methyl ethyl ketone, ether solvents such as diethyl ether, diisopropyl ether, tetrahydrofuran, 1,4-dioxane and ethylene glycol monomethylether, and the like. Examples of aromatic hydrocarbon solvents include toluene, xylene, mesitylene, cyclohexylbenzene, isopropylbiphenyl and the like. Examples of halogen solvents include methylene chloride, 1,1,2-trichloroethane, chloroform and the like. Further examples of solvents include anisole, 2-ethylhexane, sec-buthylether, 2-pentanol, 2-methyltetrahydrofuran, 2-propylene glycol monomethylether, 2,3-dimethyl-1,4-dioxane, sec-butylbenzene, 2-methylcyclohexylbenzene, and the like. Among them, toluene and tetrahydrofuran are preferred in terms of boiling point and solubility.

In the near-infrared absorbing composition of the present invention, at least one of the solvents has the structure of the following general formula (3) and a molecular weight of 190 or less.

General Formula (3)

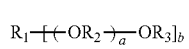

In the general formula (3), $R_1$ is a hydrogen atom or a monovalent to tetravalent organic group, $R_2$ is an alkylene group of 2 to 4 carbon atoms, $R_3$ is a hydrogen atom, an alkyl group or an acyl group, and a is an integer of 0 to 10 and b is an integer of 1 to 4. Preferably, a is an integer of 1 to 10. When b is 2 or more, the structures in the parentheses may be same or different.

Among the compounds represented by the general formula (3), compounds having b of 1 is preferred.

Further, in the general formula (3), as long as the molecular weight is equal to or less than 190, $R_1$ may be a hydrogen atom, an acyl group of 2 to 10 carbons, a linear, branched or cyclic alkyl group of 1 to 10 carbons, an aryl or aralkyl group of 6 to 10 carbons, in which at least one hydrogen atom bonded to a carbon atom of the alkyl group may be substituted with a halogen atom, a hetero atom or an aromatic ring. $R_2$ is an alkylene group of 2 to 4 carbons, and n is 1 to 10. The number of carbons of the acyl group is preferably 2 to 10. The number of carbons of the alkyl group is preferably 1 to 15. The number of carbons of the aryl or aralkyl group is preferably 6 to 20. The number of carbons of the alkylene group represented by $R_2$ is preferably 2 or 3, more preferably 2.

In the general formula (3), the acyl groups that $R_1$ can represent also include divalent acid groups derived from a dicarboxylic acid, and examples thereof include a 2-ethylbutanoyl group, a (meth)acryloyl group, a propionyl group, a butyryl group, a valeryl group, an isovaleryl group, a hexanoyl group and a heptanedioyl group. Among them, a (meth)acryloyl group and a 2-ethylhexanoyl group are preferred. Examples of the alkyl groups that $R_1$ can represent include a methyl group, an ethyl group, a propyl group, a butyl group, an amyl group, a hexyl group and a nonyl group. Among them, a methyl group and a lauryl group are preferred. Preferred examples of the aryl or aralkyl groups that $R_1$ can represent are a phenyl group and a 4-nonylphenyl group. Suitable examples of the alkylene groups that $R_2$ can represent are an ethylene group, a propylene group, a butylene group and a tetramethylene group. With these groups, it is possible to remarkably improve the solubility and dispersibility for copper-containing phosphate resin.

Exemplary compounds of solvents that can be used for the present invention are shown below.

1) PGMEA: Propylene glycol monomethyl ether acetate (molecular weight: 132)
2) PGEEA: propylene glycol monoethyl ether acetate (molecular weight: 146)
3) PGBEA: Propylene glycol monobutyl ether acetate (molecular weight: 174)
4) Ethylene glycol diacetate (molecular weight: 146)
5) Ethylene glycol diglycidyl ether (molecular weight: 174)
6) Ethylene glycol monomethyl ether acetate (molecular weight: 118)
7) Ethylene glycol monoethyl ether acetate (molecular weight: 132)
8) Ethylene glycol monobutyl ether acetate (molecular weight: 160)
9) Ethylene glycol dibutyl ether (molecular weight: 174)
10) Ethylene glycol monoacetate (molecular weight: 104)
11) Ethylene glycol monoisopropyl ether (molecular weight: 104)
12) Ethylene glycol monoethyl ether (molecular weight: 90)
13) Ethylene glycol monomethoxymethyl ether (molecular weight: 106)
14) Glycerin 1,3-diacetate (molecular weight: 176)
15) Glycerin 1,2-dimethyl ether (molecular weight: 120)
16) Glycerin 1,3-dimethyl ether (molecular weight: 120)
17) Glycerin 1,3-diethyl ether (molecular weight: 148)
18) 2-chloro-1,3-propanediol (molecular weight: 110)
19) 3-chloro-1,2-propanediol (molecular weight: 110)
20) Diethylene glycol ethyl methyl ether (molecular weight: 148)
21) Diethylene glycol dimethyl ether (molecular weight: 134)
22) Diethylene glycol monoethyl ether acetate (molecular weight: 176)
23) Diethylene glycol monobutyl ether (molecular weight: 162)
24) Diethylene glycol monomethyl ether (molecular weight: 120)
25) Dipropylene glycol (molecular weight: 134)
26) Dipropylene glycol monopropyl ether (molecular weight: 176)
27) Triethylene glycol (molecular weight: 150)
28) Triethylene glycol dimethyl ether (molecular weight: 178)
29) Triethylene glycol monoethyl ether (molecular weight: 178)
30) Triethylene glycol monomethyl ether (molecular weight: 164)
31) Propylene glycol (molecular weight: 76)
32) Propylene glycol monoethyl ether (molecular weight: 104)

Among the above dispersants, the dispersants of 1) to 17), 20) to 24), 26), 28) to 30) and 32) are particularly preferred.

Other Solvents

Examples of other solvents that can be used in combination with the solvent having the structure of the general formula (3) include: ether-based compounds having a molecular weight of more than 190 such as dioxyethylene lauryl ether, trioxyethylene lauryl ether, tetraoxyethylene lauryl ether, pentaoxyethylene lauryl ether, hexaoxyethylene lauryl ether, heptaoxyethylene lauryl ether, octaoxyethylene lauryl ether, nonaoxyethylene lauryl ether, decaoxyethylene lauryl ether, undecaoxyethylene lauryl ether, dodecaoxyethylene lauryl ether, trideca oxyethylene lauryl ether and tetradecaoxyethylene lauryl ether; diethylene glycol dimethacrylate (NK ester 2G, Shin Nakamura Chemical Co., Ltd., molecular weight: 242); triethylene glycol dimethacrylate (molecular weight 286); polyethylene glycol #200 dimethacrylate (NK ester 4G, Shin Nakamura Chemical Co., Ltd., molecular weight: 330); tripropylene glycol propyl ether; triethylene glycol bis(2-ethylhexanate) (Across Corp.); 1,3-butylene glycol dimethacrylate; and the like.

It is preferred that the percentage of the solid component in the near-infrared absorbing composition is within the range of 5 mass % to 30 mass %. This is because the concentration of the solid component (e.g. copper complex particles) becomes suitable, particle aggregation is reduced while the composition is in storage, and it becomes possible to achieve better stability over time (dispersion stability and near-infrared absorption performance of the copper complex particles). It is more preferred that the percentage is within the range of 10 mass % to 20 mass %.

Near-Infrared Absorption Adjuster

In terms of spectroscopic property, it is preferred that the near-infrared absorbing composition of the present invention contains at least one near-infrared absorption adjuster having an absorption maximum wavelength of 650 nm to 800 nm as an additive for adjusting the absorption waveform. Preferred near-infrared absorption adjusters that can be used for the present invention are near-infrared absorbing dyes that have a maximum absorption wavelength within the wavelength range of 650 nm to 800 nm.

Examples of such near-infrared absorbing dyes suitable for the present invention include cyanine dyes, squarylium dyes, croconium dyes, azo dyes, anthraquinone dyes, naphthoquinone dyes, phthalocyanine dyes, naphthalocyanine dyes, quatenylene dyes, dithiol metal complex dyes and the like. Among them, phthalocyanine dyes, naphthalocyanine dyes and quaterrylene dyes are particularly preferred since they sufficiently absorb near infrared rays, have high visible light transmittance and have high heat resistance.

Specific examples of phthalocyanine compounds include the compounds described in JP-A 2000-26748, JP-A 2000-63691, JP-A 2001-106689, JP-A 2004-149752, and JP-A 2004-18561, JP-A 2005-220060, JP-A 2007-169343, JP-A 2016-204536, JP-A 2016-218167 and the like, which can be synthesized according to the methods described in these publications.

Specific examples of quaterrylene dyes include the compounds described in JP-A 2008-009206 and JP-A 2011-225608, which can be synthesized according to the methods described in these publications.

The above-described near-infrared absorbing dyes are also available as commercial products. Examples of such products include, in their product names, FDR002, FDR003, FDR004, FDR005, FDN001 (Yamada Chemical Industry Co., Ltd.), EXCOLOR TX-EX720, EXCOLOR TX-EX708K (Nippon Shokubai Co., Ltd.), Lumogen IR765, Lumogen IR788 (BASF Corp.), ABS694, IRA735, IRA742, IRA751, IRA764, IRA788, IRA800 (Exciton Corp.), Epolight 5548, Epolight 5768 (Aako Corp.), VIS680E, VIS695A, NIR700B, NIR735B, NIR757A, NIR762A, NIR775B, NIR778A, NIR783C, NIR783I, NIR790B, NIR795A (QCR solutions, Inc.), DLS740A, DLS740B, DLS740C, DLS744A, DLS745B, DLS771A, DLS774A, DLS774B, DLS775A, DLS775B, DLS780A, DLS780C, DLS782F (Crystalin Corp.), B4360, B4361, D4773, D5013 (Tokyo Chemical Industry Co., Ltd.) and the like.

The amount of the near-infrared absorbing dye added is preferably within the range of 0.01 mass % to 0.1 mass % with respect to 100 mass % of the near-infrared absorbing agent in the near-infrared absorbing composition.

When the amount of the near-infrared absorbing dye added is equal to or 0.01 mass % with respect to 100 mass % of the near-infrared absorbing agent, it is possible to sufficiently increase the near-infrared absorption. When it is equal to or less than 0.1 mass %, the visible light transmittance of the near-infrared absorbing composition is not impaired.

UV Absorbing Agent

In terms of spectroscopic property and light resistance, it is preferred that the near-infrared absorbing composition of the present invention contains an ultraviolet (UV) absorbing agent in addition to the near-infrared absorbing agent and the solvent.

The UV absorbing agent is not particularly limited, and examples thereof include benzotriazole-based UV absorbing agents, benzophenone-based UV absorbing agents, salicylate-based UV absorbing agents, cyanoacrylate-based UV absorbing agents, triazine-based UV absorbing agents, and the like.

Examples of benzotriazole-based UV absorbing agents include 5-chloro-2-(3,5-di-sec-butyl-2-hydroxylphenyl)-2H-benzotriazole and (2-2H-benzotriazol-2-yl)-6-(linear and side chain dodecyl)-4-methylphenol and the like. Benzotriazole-based UV absorbing agents are also available as commercial products. Examples thereof are TINUVIN series such as TINUVIN 109, TINUVIN 171, TINUVIN 234, TINUVIN 326, TINUVIN 327, TINUVIN 328 and TINUVIN 928, all of which are commercial products of BASF.

Examples of benzophenone-based UV absorbing agents include 2-hydroxy-4-benzyloxybenzophenone, 2,4-benzyloxybenzophenone, 2,2'-dihydroxy-4-methoxybenzophenone, 2-hydroxy-4-methoxy-5-sulfobenzophenone, bis(2-methoxy-4-hydroxy-5-benzoylphenylmethane), and the like.

Examples of salicylate-based UV absorbing agents include phenyl salicylate, p-tert-butyl salicylate, and the like.

Examples of cyanoacrylate-based UV absorbing agents include 2'-ethylhexyl-2-cyano-3,3-diphenyl acrylate, ethyl-2-cyano-3-(3',4'-methylenedioxyphenyl)-acrylate, and the like.

Examples of triazine-based UV absorbing agents include 2-(2'-hydroxy-4'-hexyloxyphenyl)-4,6-diphenyltriazine and the like. Examples of commercially available triazine-based UV absorbing agents include TINUVIN 477 (BASF).

The amount of UV absorbing agent added is preferably within a range of 0.1 mass % to 5.0 mass % with respect to 100 mass % of the near-infrared absorbing agent in the near-infrared absorbing composition.

When the amount of UV absorbing agent added is equal to or greater than 0.1 mass % with respect to 100 mass % of the near-infrared absorbing agent, the light resistance can be sufficiently increased. When it is equal to or less than 5.0 mass %, the visible light transmittance of the near infrared absorbing composition is not impaired.

Near-Infrared Absorbing Film and Applicable Fields Thereof

One of the features of the present invention is to form a near-infrared absorbing film by using the near-infrared absorbing composition of the present invention.

The near-infrared absorbing film of the present invention is formed by adding a matrix resin to the near-infrared absorbing composition of the present invention so as to allow, for example, fine particles of a metal complex, and if necessary, a phosphonate metal complex such as phosphonate copper complex to be dispersed in the matrix resin. Further, as an additive for adjusting the absorption waveform, at least one of the above-described near-infrared dyes having a maximum absorption wavelength within the wavelength range of 650 nm to 800 nm can be added.

The near-infrared absorbing film-forming liquid having the above configuration is applied onto a substrate by spin coating or wet coating with a dispenser to form a near-infrared absorbing film. Then, the coating film is subjected to a predetermined heat treatment, thereby curing the coating film to form a near infrared absorbing film.

The matrix resin used for forming the near-infrared absorbing film is transparent to visible light and near-infrared rays and can disperse fine particles of the metal complex and the copper phosphonate complex therein. The metal complex and the copper phosphonate complex are substances having a relatively low polarity and are well dispersed in hydrophobic material. Accordingly, a resin having an acrylic group, an epoxy group or a phenyl group can be used as the matrix resin for forming the near-infrared absorbing film. Among them, it is particularly preferred to use a resin having a phenyl group as the matrix resin of the near-infrared absorbing film. In this case, the matrix resin of the near-infrared absorbing film has high heat resistance. In addition, polysiloxane silicone resin is resistant to degradation by heat, has high transparency to visible rays and near infrared rays, and has high heat resistance. That is, polysiloxane silicone resin has advantageous properties as a material of an image sensor for a solid imaging element. Therefore, it is also preferred to use polysiloxane as the matrix resin of the near-infrared absorbing film. Polysiloxane that can be used as the matrix resin for the near-infrared absorbing film is available as a commercial product, and examples thereof include KR-255, KR-300, KR-2621-1, KR-211, KR-311, KR-216, KR-212 and KR-251, which are silicone resins manufactured by Shin-Etsu Chemical Co., Ltd.

Other Additives

Other additives can be used in the near-infrared absorbing film of the present invention within the range that does not impair the intended advantageous effects of the present invention. Examples of such additives include sensitizers, cross-linking agents, curing accelerators, fillers, thermosetting accelerators, thermal polymerization inhibitors, plasticizers and the like. Further, adhesion promoters for adhesion to the surface of a substrate and other auxiliary agents (e.g. conductive particles, fillers, defoamers, flame retardants, leveling agents, peeling accelerators, antioxidants, fragrances, surface tension adjusting agents, chain transfer agents, etc.) may be used in combination.

By suitably adding these components, it is possible to adjust desired properties such as stability and physical properties of the near-infrared absorbing film.

For these components, for example, paragraphs 0229 to 0260 of JP-A 2012-003225, paragraphs 0101 to 0102 of JP-A 2008-250074 and paragraphs 0103 to 0104 of JP-A 2008-250074, paragraphs 0107 to 0109 of JP-A 2008-250074 and the like can be used as references.

The near-infrared absorbing composition of the present invention can be a wet coating solution in the form of liquid. Therefore, for example, a near-infrared absorbing film, e.g. a near-infrared cutoff filter, can be readily produced by a simple process, for example, by forming a film by spin coating.

Application to Image Sensor for Solid Imaging Element

For example, the near-infrared absorbing film of the present invention is suitable as a component of a luminous efficiency correction member for CCD, CMOS or other light receiving elements, a photometric member, a heat ray absorbing member, a composite optical filter, a lens member (glasses, sunglasses, goggles, optical systems, optical waveguide systems), a fiber member (optical fiber), a noise cutoff member, a display cover or a display filter such as a plasma display front plate, a projector front plate, a light source heat ray cutoff member, a color tone correcting member, an light brightness regulator, an optical element (optical amplification element, wavelength conversion element, etc.), a faraday element, an optical communication functional device such as an isolator, an optical disk element, and the like.

Regarding the use applications, the near-infrared absorbing composition of the present invention is particularly used for an image sensor for a solid imaging element, for example, as a near-infrared absorbing cutoff filter on the light receiving side of a solid imaging element substrate (e.g. a near-infrared cutoff filter for wafer-level lenses) or a near-infrared cutoff filter on the back side (opposite side from the light receiving side) of a solid imaging element substrate.

By using the near-infrared absorbing film of the present invention to an image sensor for a solid imaging element, it is possible to improve the visible range transmittance, the near-infrared range absorption efficiency, the resistance to heat and humidity, and the like.

The near-infrared absorbing film (near-infrared cutoff filter) of the present invention is provided on an image sensor for a solid imaging element.

FIG. 1 is a schematic cross-sectional view showing the configuration of a camera module equipped with a solid imaging element. The solid imaging element has an infrared cutoff filter which is the near-infrared absorbing film of the present invention.

A camera module 1 shown in FIG. 1 is connected to a circuit board 12 as a mounting board via solder balls 11 as connection members.

More specifically, the camera module 1 includes a solid imaging element substrate 10 in which an imaging element portion 13 is provided on a first main surface of a silicone substrate, a flattening layer 8 disposed on the first main surface (light receiving side) of the solid imaging element substrate 10, a near-infrared cutoff filter (near-infrared absorbing film) 9 disposed on the flattening layer 8, a glass substrate 3 (light permeable substrate) disposed above the near-infrared cutoff filter 9, a lens holder 5 with an imaging lens 4 disposed above the glass substrate 3, and an optical and magnetic shield 6 surrounding the solid imaging element substrate 10 and the glass substrate 3. These members are bonded by adhesives 2, 7.

The present invention is a method for manufacturing a camera module that includes a solid imaging element substrate and an infrared cutoff filter disposed on the light receiving side of the solid imaging element substrate. By applying the above-described infrared absorbing liquid composition of the present invention by spin coating, it is possible to form a near-infrared absorbing film on the light receiving side of the solid imaging element substrate.

In the camera module 1, the infrared cutoff filter 9 is formed, for example, by applying the near-infrared absorbing composition of the present invention onto the flattening layer 8 by spin coating so that the near-infrared absorbing film is formed.

The camera module 1 is configured such that incident light L from the outside passes through the imaging lens 4, the glass substrate 3, the infrared cutoff filter 9 and the flattening layer 8 in the written order and then reaches the imaging element portion of the solid imaging element substrate 10.

The camera module 1 is connected to the circuit board 12 at a second main surface of the solid imaging element substrate 10 via solder balls 11 (connecting material).

EXAMPLES

Hereafter, the present invention will be described specifically by referring to examples, however, the present invention is not limited thereto. The indications of "part" and "%", which are used in the examples, represent respectively "part(s) by mass" and "mass %" unless otherwise particularly mentioned. Further, each step is performed at room temperature (25° C.) unless otherwise specified.

Example 1

Preparation of Near-Infrared Absorbing Composition
Preparation of Near-Infrared Absorbing Composition 1
A near-infrared absorbing composition 1 was prepared according to the following method.
Copper acetate (16.54 g) and 661.46 g of tetrahydrofuran (abbreviated as THF) as the solvent thereof were mixed. The copper acetate was dissolved using an ultrasonic irradiator.

The solution was filtrated to remove residual copper acetate. A copper acetate solution (678 g) was thus obtained.

Then, to 678 g of the copper acetate solution, a solution of 43.86 g of Exemplary Compound 1 of the present invention in 80.0 g of THF was added over 30 minutes while stirring the solution. After the mixture solution was further stirred for 16 hours at room temperature, 238.97 g of toluene was added, and THF as the solvent was evaporated in the environment of 55° C. to 90° C. over 3 hours until the solid content became 10 mass %. The near-infrared absorbing composition 1 (251.0 g) was thus prepared.

Preparation of Near-Infrared Absorbing Composition 2

A near-infrared absorbing composition 2 was prepared in the same manner as the preparation of the near-infrared absorbing composition 1 except that equimolar nickel acetate was used instead of copper acetate.

Preparation of Near-Infrared Absorbing Composition 3

A near-infrared absorbing composition 3 was prepared in the same manner as the preparation of the near-infrared absorbing composition 1 except that equimolar cobalt acetate was used instead of copper acetate.

Preparation of Near-Infrared Absorbing Compositions 4 to 14

Near-infrared absorbing compositions 4 to 14 were prepared in the same manner as the preparation of the near-infrared absorbing composition 1 except that equimolar exemplary compounds listed in Table IV were respectively used instead of Exemplary Compound 1.

Preparation of Near-Infrared Absorbing Compositions 15 to 23

In the preparation of the near-infrared absorbing composition 1, 27% of Exemplary Compound 1 was changed respectively to the equimolar exemplary compounds listed in Table V as the compound of the general formula (I). Solutions of the exemplary compounds in 35 ml of THF were added dropwise to the copper acetate solution over 15 minutes. After stirring for 30 minutes, solutions of equimolar ligand compounds in Table V instead of the other 73% in 45 ml of THF were further added dropwise respectively over 15 minutes. After stirring for 16 hours at room temperature, 238.97 g of anisole was added, and THF as the solvent was evaporated in the environment of 55° C. to 90° C. over 3 hours until the solid content became 10 mass % The near-infrared absorbing compositions 15 to 23 were thus prepared.

The ligand compound (*1) in Table V used in the preparation of the near-infrared absorbing composition 23 was described as A-26 in Table 1 in paragraph 0021 of JP-A 2015-43063.

Preparation of Near-Infrared Absorbing Composition 24

In the preparation of the near-infrared absorbing composition 4, Exemplary Compound 40 was changed to Exemplary Compound 91. After it was added dropwise to the copper acetate solution and stirred for 16 hours at room temperature, 9.04 g of near-infrared absorbing dye FRD004 (maximum absorption wavelength: 716 nm, Yamada Chemical Co., Ltd.) was added as the near-infrared absorption adjuster as listed in Table V, and 238.97 g of anisole was further added thereto. THF as the solvent was evaporated in the environment of 55° C. to 90° C. over 3 hours until the solid content became 10 mass % The near-infrared absorbing composition 24 was thus prepared.

Preparation of Near-Infrared Absorbing Composition 25

In the preparation of the near-infrared absorbing composition 17, Exemplary Compound 56 was changed to Exemplary Compound 53 as listed in Table V. After it was added dropwise to the copper acetate solution and stirred for 16 hours at room temperature, 9.04 g of near-infrared absorbing dye FRD004 (maximum absorption wavelength: 716 nm, Yamada Chemical Co., Ltd.) was added as the near-infrared absorption adjuster as listed in Table V, and 238.97 g of anisole was further added thereto. THF as the solvent was evaporated in the environment of 55° C. to 90° C. over 3 hours until the solid content became 10 mass %. The near-infrared absorbing composition 25 was thus prepared.

Preparation of Near-Infrared Absorbing Composition 26

Near-infrared absorbing composition 26 was prepared in the same manner as the preparation of the near-infrared absorbing composition 25 except as follows. Exemplary Compound 53 was changed to Exemplary Compound 57 as listed in Table V. After it was added dropwise to the acetate solution and stirred for 16 hours at room temperature, 9.04 mg of the near-infrared absorbing dye FDR004 and 21.59 mg of Lumogen IR765 (BASF) were used as the near-infrared absorption adjuster as listed in Table V.

Preparation of Near-Infrared Absorbing Composition 27

Near-infrared absorbing composition 27 was prepared in the same manner as the preparation of the near-infrared absorbing composition 21 except as follows. Exemplary Compound 77 was changed to Exemplary Compound 67 as listed in Table V. After it was added dropwise to the acetate solution and stirred for 16 hours at room temperature, 9.04 mg of the near-infrared absorbing dye FDR004 and 21.59 mg of Lumogen IR765 (BASF) were used as the near-infrared absorption regulator as listed in Table V.

Preparation of Near-Infrared Absorbing Composition 28

Near-infrared absorbing composition 28 was prepared in the same manner as the preparation of the near-infrared absorbing composition 1 except that equimolar Comparative Compound 1 was used instead of Exemplary Compound 1.

Comparative Compound 1

R: n-dodecyl group

Condition (i): $R_{21}$ to $R_{24}$=H

Z: Z-1, Z-2 (monoester percentage of 50%)

I: 3.0 m: 0

Preparation of Near-Infrared Absorbing Composition 29

A near-infrared absorbing composition 29 was prepared in the same manner as the preparation of the near-infrared absorbing composition 1 except that equimolar Comparative Compound 2 was used instead of Exemplary Compound 1.

Comparative Compound 2

R: n-dodecyl group

Condition (ii): $R_{21}$=H, $R_{22}$=methyl group, $R_{23}$=methyl group, and $R_{24}$=H Z: Z-1, Z-2 (monoester percentage of 50%)

l: 0 m: 3.0

Preparation of Near-Infrared Absorbing Composition 30

A near-infrared absorbing composition 30 was prepared in the same manner as the preparation of the near-infrared absorbing composition 1 except that the equimolar amount of combination of Comparative Compound 1+Comparative Compound 2 (composition ratio of 1:1) was used instead of Exemplary Compound 1.

Details of the near-infrared absorbing compositions thus prepared are shown in Table V.

TABLE V

| Infrared Absorbing Composition Number | Metal Species | Compound of General Formula (I) | | | Monoester Ratio (%) | Type of Ligand Compound | Type of Near-Infrared Absorption Adjuster | Remarks |
|---|---|---|---|---|---|---|---|---|
| | | Exemplary Compound Number | 1/m(E0/P0) | Z | | | | |
| 1 | Cu$^{2+}$ | 1 | 1.0/8.0 | Z-3 | — | — | — | Inventive |
| 2 | Ni$^{2+}$ | 1 | 1.0/8.0 | Z-3 | — | — | — | Inventive |
| 3 | Co$^{2+}$ | 1 | 1.0/8.0 | Z-3 | — | — | — | Inventive |
| 4 | Cu$^{2+}$ | 40 | 5.0/5.0 | Z-1, Z-2 | 98 | — | — | Inventive |
| 5 | Cu$^{2+}$ | 60 | 5.0/5.0 | Z-1, Z-2 | 18 | — | — | Inventive |
| 6 | Cu$^{2+}$ | 17 | 4.0/5.0 | Z-1, Z-2 | 20 | — | — | Inventive |
| 7 | Cu$^{2+}$ | 68 | 2.0/5.0 | Z-1, Z-2 | 95 | — | — | Inventive |
| 8 | Cu$^{2+}$ | 30 | 3.0/4.0 | Z-1, Z-2 | 50 | — | — | Inventive |
| 9 | Cu$^{2+}$ | 38 | 3.0/3.0 | Z-1, Z-2 | 60 | — | — | Inventive |
| 10 | Cu$^{2+}$ | 49 | 2.0/2.0 | Z-1, Z-2 | 50 | — | — | Inventive |
| 11 | Cu$^{2+}$ | 44 | 1.0/3.0 | Z-1, Z-2 | 70 | — | — | Inventive |
| 12 | Cu$^{2+}$ | 41 | 2.5/2.5 | Z-1, Z-2 | 60 | — | — | Inventive |
| 13 | Cu$^{2+}$ | 50 | 1.0/2.0 | Z-1, Z-2 | 50 | — | — | Inventive |
| 14 | Cu$^{2+}$ | 52 | 2.0/1.0 | Z-1, Z-2 | 50 | — | — | Inventive |
| 15 | Cu$^{2+}$ | 21 | 2.0/4.0 | Z-1, Z-2 | 60 | Methylphosphonic Acid | — | Inventive |
| 16 | Cu$^{2+}$ | 22 | 2.5/2.0 | Z-1, Z-2 | 80 | Ethylphosphonic Acid | — | Inventive |
| 17 | Cu$^{2+}$ | 56 | 2.5/2.5 | Z-1, Z-2 | 50 | Propylphosphonic Acid | — | Inventive |
| 18 | Cu$^{2+}$ | 57 | 1.0/1.5 | Z-1, Z-2 | 60 | Propylphosphonic Acid | — | Inventive |
| 19 | Cu$^{2+}$ | 58 | 1.0/2.0 | Z-1, Z-2 | 30 | Propylphosphonic Acid | — | Inventive |
| 20 | Cu$^{2+}$ | 63 | 2.0/3.0 | Z-1, Z-2 | 50 | Propylphosphonic Acid | — | Inventive |
| 21 | Cu$^{2+}$ | 77 | 2.0/2.0 | Z-1, Z-2 | 60 | Hexylphosphonic Acid | — | Inventive |
| 22 | Cu$^{2+}$ | 54 | 2.0/2.0 | Z-1, Z-2 | 40 | Butyl Phosphate | — | Inventive |
| 23 | Cu$^{2+}$ | 71 | 2.0/2.0 | Z-1, Z-2 | 50 | * 1 | — | Inventive |
| 24 | Cu$^{2+}$ | 91 | 3.0/3.0 | Z-1, Z-2 | 70 | — | FDR004 | Inventive |
| 25 | Cu$^{2+}$ | 53 | 2.0/2.0 | Z-1, Z-2 | 55 | Propylphosphonic Acid | FDR004 | Inventive |
| 26 | Cu$^{2+}$ | 57 | 1.0/1.5 | Z-1, Z-2 | 60 | Propylphosphonic Acid | * 2 | Inventive |
| 27 | Cu$^{2+}$ | 67 | 1.0/1.0 | Z-1, Z-2 | 50 | Hexylphosphonic Acid | * 2 | Inventive |
| 28 | Cu$^{2+}$ | Comparative Compound 1 | 3.0/0 | Z-1, Z-2 | 50 | — | — | Comparative |
| 29 | Cu$^{2+}$ | Comparative Compound 2 | 0/3.0 | Z-1, Z-2 | 50 | — | — | Comparative |
| 30 | Cu$^{2+}$ | Comparative Compound 1<br>Comparative Compound 2 | 3.0/0<br>0/3.0 | Z-1, Z-2 | 50 | — | — | Comparative |

* 1: A-26 in Table 1 of JP-A 2015-43063
* 2: FDR004 + Lumogen I R765

Evaluation of Near-Infrared Absorbing Compositions

The near-infrared absorbing compositions thus prepared were evaluated for particle size, visible and near-infrared transmittance and resistance to heat and moisture.

Measurement of Average Particle Size of Metal Complex Particles

Evaluation samples A were prepared by diluting the prepared near-infrared absorbing compositions 1 to 30 with toluene so that the particle concentration of the particle metal complex (solid component concentration) became 1.0 mass %.

Then, the average particle size of the evaluation samples A was measured by a dynamic light scattering method using a zeta potential and particle size measuring system ELSZ-1000ZS (Otsuka Electronics Co., Ltd.) as the measuring instrument.

The average particle size, which was measured by the above-described method immediately after preparation, was graded according to the following criteria.
  AA: Average particle size is equal to or less than 50 nm.
  BB: Average particle size is within the range of more than 50 nm to 100 nm.
  CC: Average particle size is within the range of more than 100 nm to 200 nm.
  DD: Average particle size is greater than 200 nm.

Evaluation of Spectroscopic Transmittance

The spectroscopic transmittance within the wavelength range of 300 nm to 1200 nm of the evaluation samples A, which were prepared for the measurement of the average particle size, was measured using a spectrometer V-570 (JASCO Corp.) as the measuring instrument. Then, the spectroscopic transmittance was evaluated at 500 nm for the visible range and 700 nm and 800 nm for the near-infrared range.

Evaluation of Transmittance in Visible Range

The transmittance at 500 nm of the near-infrared absorbing compositions, which was measures by the above-described method, was graded according to the following criteria to evaluate the transmittance in the visible range.
  AA: Maximum transmittance is equal to or greater than 95%.
  BB: Maximum transmittance is from 90% to less than 95%.
  CC: Maximum transmittance is from 80% to less than 90%.
  DD: Maximum transmittance is less than 80%.

Evaluation of Transmittance in Near-Infrared Range

The transmittance at 700 nm and 800 nm of the near-infrared absorbing compositions, which was measures by the above-described method, was graded according to the following criteria to evaluate the transmittance in the near-infrared range.
  AA: Maximum transmittance is less than 5%.
  BB: Maximum transmittance is from 5% to less than 10%.
  CC: Maximum transmittance is from 10% to less than 20%.
  DD: Maximum transmittance is equal to or grater than 20%.

Evaluation of Resistance to Heat and Moisture

Crude liquid (5 ml) of each of the near-infrared absorbing compositions and 0.03 g of pure water were charged and sealed in a glass container filled with nitrogen gas. The container was stored in a thermostat bath at 65° C. for 5 days while the mixture was stirred. Thereafter, the mixture was diluted with toluene as described above so that the concentration of the near-infrared absorbing composition in the stored solution became 1.0 mass %. Toluene-diluted samples B after storage were thus prepared.

The maximum transmittance $T_{max2}$ in the visible range (400 nm to 750 nm) of the samples B after storage was measured in the same manner as described above using a spectrophotometer V-570 (JASCO Corp.)

Then, the maximum transmittance $T_{max1}$ of the samples A immediately after preparation was measured in the same manner. The decrease ($T_{max2}-T_{max1}$) of the visible transmittance from the maximum transmittance $T_{max1}$ to the maximum transmittance $T_{max2}$ of the samples B after storage was determined. The visible transmittance after storage was graded according to the following criteria, which was used as a measure of resistance to heat and moisture.

AA: Decrease of visible transmittance is less than 1.0%.
BB: Decrease of visible transmittance is from 1.0% to less than 3.0%.
CC: Decrease of visible transmittance is from 3.0% to less than 5.0%.
DD: Decrease of visible transmittance is equal to or greater than 5.0%.

The results are shown in Table VI.

As can be seen from the results shown in Table VI, the inventive near-infrared absorbing compositions, in which the inventive exemplary compounds are used, have small average particle size of metal complex particles, good spectroscopic properties, high transmittance in the visible range (500 nm), low transmittance in the near-infrared range (700 nm, 800 nm) and good near-infrared light cutoff performance compared to the comparative examples. In addition, the inventive near-infrared absorbing compositions exhibit good stability even when stored in the presence of water in a high temperature environment for a long time compared to the comparative examples.

As demonstrated by the near-infrared absorbing compositions 15 to 21, the overall properties as described above are further improved when the specific phosphonic acid compounds are added. Furthermore, as demonstrated by the near-infrared absorbing compositions 24 to 27, the overall properties as described above are improved when the specific near-infrared absorbing dyes are added.

The inventive near-infrared absorbing compositions exhibited a less decrease of the average transmittance in the visible range when stored in a high temperature environment. This means less degradation of transmittance that is caused by aggregation of the metal complex particles and the like due to heat and moisture. That is, the inventive

TABLE VI

| Infrared Absorbing Composition Number | Average Particle Size | Transmittance 1 (Visible Region) at 500 nm | Transmittance 2 (Near-Infrared Region 1) at 700 nm | Transmittance 3 (Near-Infrared Region 2) at 800 nm | Resistance to Heat and Moisture | Remarks |
|---|---|---|---|---|---|---|
| 1 | CC | CC | BB | BB | CC | Inventive |
| 2 | CC | CC | CC | CC | CC | Inventive |
| 3 | CC | CC | CC | CC | CC | Inventive |
| 4 | BB | BB | BB | BB | BB | Inventive |
| 5 | BB | BB | BB | BB | BB | Inventive |
| 6 | AA | AA | BB | BB | CC | Inventive |
| 7 | AA | AA | BB | BB | BB | Inventive |
| 8 | AA | AA | BB | BB | BB | Inventive |
| 9 | AA | AA | BB | BB | BB | Inventive |
| 10 | AA | AA | BB | BB | BB | Inventive |
| 11 | AA | AA | BB | BB | BB | Inventive |
| 12 | AA | AA | BB | BB | BB | Inventive |
| 13 | AA | AA | BB | BB | BB | Inventive |
| 14 | AA | AA | BB | BB | BB | Inventive |
| 15 | BB | AA | BB | AA | CC | Inventive |
| 16 | AA | AA | BB | AA | CC | Inventive |
| 17 | AA | AA | BB | AA | BB | Inventive |
| 18 | AA | AA | BB | AA | BB | Inventive |
| 19 | AA | AA | BB | AA | BB | Inventive |
| 20 | AA | AA | BB | AA | BB | Inventive |
| 21 | AA | AA | BB | AA | BB | Inventive |
| 22 | BB | AA | BB | BB | BB | Inventive |
| 23 | BB | AA | BB | BB | BB | Inventive |
| 24 | AA | AA | AA | BB | BB | Inventive |
| 25 | AA | AA | AA | AA | BB | Inventive |
| 26 | AA | AA | AA | AA | BB | Inventive |
| 27 | AA | AA | AA | AA | BB | Inventive |
| 28 | BB | BB | BB | BB | DD | Comparative |
| 29 | DD | DD | CC | BB | BB | Comparative |
| 30 | CC | BB | BB | BB | DD | Comparative | near-infrared absorbing compositions have particularly good stability in storage in a hot and humid environment.

Example 2

Quantitative Determination of Acetic Acid

Each of the near-infrared absorbing compositions 1 to 27 prepared in Example 1 was added to toluene and ultrapure water and stirred for 10 minutes. Thereafter, the aqueous layer was collected by centrifugation and filtrated with a 0.45 μm filter. Thereafter, acetic ions were detected with a capillary electrophoretic device (CAPI-3300, Otsuka Electronics Co., Ltd.), and the content (mole) thereof was determined using a calibration curve.

Then, the content (mol %) of acetic acid with respect to the metal (mole) in the near-infrared absorbing compositions, which was separately measured (by IPC emission spectrometric analysis), was determined. It was confirmed that the acetic acid content was within the range of 1 mol % to 100 mol % in all of the near-infrared absorbing compositions 1 to 27.

Measurement Example

An example of the results of measuring acetic acid content by the above-described method is shown below.

The near-infrared absorbing compositions 18 prepared in Example 1 was added to toluene and ultrapure water and stirred for 10 minutes. Thereafter, the aqueous layer was collected by centrifugation and filtrated with a 0.45 μm filter. Thereafter, acetic ions were detected with a capillary electrophoretic device (CAPI-3300, Otsuka Electronics Co., Ltd.), and the acetic acid was quantitatively determined using a calibration curve. The acetic acid content with respect to the metal (copper in this case) was 82 mol %.

Next, to determine the effect of acetic acid content, Samples 18-2, 18-3 and 18-4 were prepared from the near-infrared absorbing composition 18 by adding acetic acid. The acetic acid content was adjusted respectively to 92 mol % (18-2), 102 mol % (18-3) and 132 mol % (18-4). The original sample was referred to as Sample 18-1. With regard to resistance to heat and moisture evaluated by the method described in Example 1, Samples 18-1 and 18-2 exhibited excellent performance (evaluation grade AA) in the decrease of visible transmittance, and Sample 18-3 exhibited good performance (evaluation grade BB). In contrast, Sample 18-4 exhibited a moderate decrease in visible transmittance, and the evaluation grade was CC.

Example 3

Near-infrared absorbing compositions 19-a, 19-b and 19-c were prepared from the near-infrared absorbing composition 19 prepared in Example 1 by distilling away the solvent so that the solid concentration became respectively 20 mass %, 30 mass % and 35 mass %. The outer appearance of the prepared samples was visually observed. The near-infrared absorbing compositions 19-a and 19-b were smooth liquid. In contrast, thixotropic nature and an increase of the viscosity was observed in the near-infrared absorbing composition 19-c.

Example 4

Manufacture of Near-Infrared Absorbing Film

Coating liquids for forming near-infrared absorbing film were prepared by adding polysiloxane silicone resin (KR-255, Shin-Etsu Chemical Co., Ltd.) to each of the near-infrared absorbing compositions prepared in Example 1 and stirring the mixtures. Near-infrared absorbing films 1 to 27 were manufactured by applying the coating liquids thus prepared onto a substrate by spin coating.

Then, the near-infrared absorbing films were subjected to a predetermined heat treatment so that the films were cured. Near-infrared cutoff filters 1 to 27 applicable to an image sensor for a solid imaging element were thus manufactured.

The near-infrared cutoff filters thus manufactured were subjected to evaluation of the visible transmittance and near-infrared transmittance in the form of film in the same manner as described in Example 1. It was confirmed that the same advantageous effects can be obtained even in the form of film.

Further, the near-infrared cutoff filters thus manufactured were stored in an environment of 80° C. and 60% RH for one week, and then subjected to the same measurement. It was confirmed that no haze occurred in the near-infrared cutoff filters using the near-infrared absorbing films of the present invention, and the spectroscopic properties were at the same level as those before the storage.

INDUSTRIAL APPLICABILITY

The near-infrared absorbing composition of the present invention has high near-infrared light absorption performance, good dispersion of the metal complex, particularly, the copper complex, good dispersion stability when exposed to water (resistance to moisture), and is suitably applicable to infrared cutoff filters for CCD and COMS image sensors, which are solid imaging elements applicable to video cameras, digital still cameras, camera phones and the like.

REFERENCE SIGNS LIST

1 Camera module
2, 7 Adhesive
3. Glass substrate
4. Imaging lens
5. Lens holder
6. Light and magnetic shield
8. Flattening layer
9. Near-infrared absorbing film (near-infrared cutoff filter)
10. Solid imaging element substrate
11. Solder balls
12. Circuit board
13. Imaging element portion

The invention claimed is:

1. A near-infrared absorbing composition, comprising: a near-infrared absorbing agent; and a solvent,
wherein the near-infrared absorbing agent comprises at least one of the following Component (A) and Component (B):
Component (A): a component composed of a compound having a structure of the following general formula (I) and a metal ion; and
Component (B): a component composed of a metal complex that is a reaction product of the compound having the structure of the following general formula (I) and a metal compound,

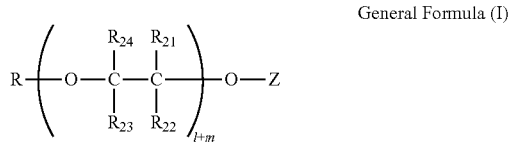

General Formula (I)

in the general formula (I), R is an alkyl group of 1 to 20 carbons or an aryl group of 6 to 20 carbons, in which R may have a substituent, and z is a structural unit selected from the following formulae (Z-1) to (Z-3),

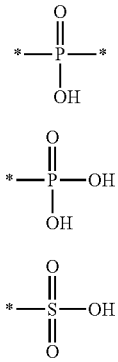

the asterisk in the formulae (Z-1) to (Z-3) represents a bonding site that is bonded to O of the general formula (I), $R_{21}$ to $R_{24}$ each is a hydrogen atom or an alkyl group of 1 to 4 carbons, the compound having the structure of the general formula (I) concurrently has at least one moiety satisfying the following Condition (i) and at least one moiety satisfying the following Condition (ii):

Condition (i): $R_{21}$ to $R_{24}$ are all hydrogen atoms;

Condition (ii): at least one of $R_{21}$ to $R_{24}$ is an alkyl group of 1 to 4 carbons, in the general formula (I), l is a number of the moiety satisfying the Condition (i) and is from 1 to 10, and m is a number of the moiety satisfying the Condition (ii) and is from 1 to 10, and the composition further comprises a phosphonic acid compound having the following structure:

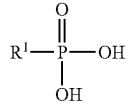

wherein $R^1$ is a branched, linear or cyclic alkyl, alkenyl, alkynyl, aryl or aryl group of 1 to 30 carbons, and at least one hydrogen atom of $R^1$ is optionally substituted with a halogen atom, an oxyalkyl, polyoxyalkyl, oxyaryl, oxyaryl, polyoxyaryl, acyl, aldehyde, carboxyl or hydroxyl group, or a group having an aromatic ring.

2. The near-infrared absorbing composition according to claim 1, wherein metal of the metal ion or the metal complex is copper.

3. The near-infrared absorbing composition according to claim 1, wherein the compound having the structure of the general formula (I) is a compound having a structure of the following general formula (II),

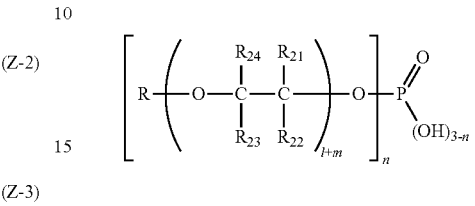

General Formula (II)

in the general formula (II), R, $R_{21}$ to $R_{24}$, and m are as defined in the general formula (I), and n is one or two, and when n is two, structures in parentheses may be same or different.

4. The near-infrared absorbing composition according to claim 1, wherein the compound having the structure of the general formula (I) has a monoester and a diester, and a molar ratio of the mono ester is within the range of 20% to 95%.

5. The near-infrared absorbing composition according to claim 1, wherein the general formula (I) concurrently has at least one moiety satisfying the following Condition (i) and at least one moiety satisfying the following Condition (iii):

Condition (i): $R_{21}$ to $R_{24}$ are all hydrogen atoms; and

Condition (iii): one of $R_{21}$ to $R_{24}$ is an alkyl group of 1 to 4 carbons, and the other three are hydrogen atoms.

6. The near-infrared absorbing composition according to claim 1, wherein l and m in the general formula (I) are each within a range of 1 to 3.

7. The near-infrared absorbing composition according to claim 1, wherein an average particle size of the metal complex is equal to or less than 50 nm.

8. The near-infrared absorbing composition according to claim 1, further comprising a near-infrared absorption adjuster having an maximum absorption wavelength within a wavelength range of 650 nm to 800 nm.

9. The near-infrared absorbing composition according to claim 1, comprising an acetic acid within a range of 1 mol % to 100 mol % with respect to metal of the metal ion or the metal compound, in addition to the near-infrared absorbing agent and the solvent.

10. A near-infrared absorbing film using the near-infrared absorbing composition according to claim 1.

11. An image sensor for a solid imaging element, comprising the near-infrared absorbing film according to claim 10.

* * * * *